United States Patent [19]

Flisak et al.

[11] Patent Number: 5,110,959
[45] Date of Patent: May 5, 1992

[54] PROCESS FOR PREPARATION OF EPOXY ESTERS AND INTERMEDIATES PREPARED THEREBY

[75] Inventors: Joseph R. Flisak, Audubon, Pa.; Paul G. Gassman, St. Paul, Minn.; Ivan Lantos, Wayne; Wilford L. Mendelson, King of Prussia, both of Pa.

[73] Assignee: Smithkline Beckman Corp., Philadelphia, Pa.

[21] Appl. No.: 366,059

[22] Filed: Jun. 14, 1989

[51] Int. Cl.[5] .................. C07D 303/38; C07D 303/00
[52] U.S. Cl. .................................... 549/513; 549/539; 549/549
[58] Field of Search .................. 549/513, 539, 549

[56] References Cited

PUBLICATIONS

Rucker, Arch. Pharm., 317, 561 (1984).
DeBoer et al., J. Org. Chem., 39, 77 (1974).
Levine, S., J. Org. Chem., 31, 3189 (1966).
Yokayama et al., Bull. Chem. Soc. Japan, 38, 1498 (1965).
Payne et al., J. Org. Chem. 24, 284 (1959).
Walton, J. Org. Chem., 22, 1161 (1957).
Nagesam et al., Acta Cienc. Indica Ser. Chem., 10, 165 (1984).
Profft et al., J. Prakt. Chem., 19, 192 (1963).
Tsatsas et al., Prakt. Akad. Athenon, 35, 418 (1960).
Julia et al., Agnew. Chem. Int. Ed. Engl., 19, 929 (1980).
Julia et al., J. Chem. Soc. Perkin Trans. I, 1317 (1982).
Julia et al., Anales De Quimica, 79, 102 (1983).
Colonna et al., Tetrahedron, 39, 1635 (1983).
Banfi et al., Tetrahedron, 40, 5207 (1984).
Gleason et al., J. Med. Chem., 30, 959 (1987).
Annunziata, Synthetic Communications, 9, 171 (1979).
Ahmed Abdel-Magid et al., Tet. Lett., 25, 3273 (1984).
Marsman et al., J. Org. Chem., 44, 2312 (1979).
Banfi et al., Syn. Comm., 13, 1049 (1983).
Perchonock et al., J. Med. Chem., 29, 1442 (1986).
Murphy et al., J. Med. Chem. 28, 1145 (1985).
Gowan et al., *Name Index of Organic Reactions*, 1960, p. 12, No. 35.

Primary Examiner—C. Warren Ivy
Assistant Examiner—Raymond Covington
Attorney, Agent, or Firm—Charles M. Kinzig; Stuart R. Suter; Edward T. Lentz

[57] ABSTRACT

This invention relates to a process for preparing epoxy esters, and intermediates prepared by this process, in particular, to a process which produces non-racemic epoxy esters which are of use as intermediates in the preparation of pharmaceutical compounds.

37 Claims, 1 Drawing Sheet

Figure 1

PROCESS FOR PREPARATION OF EPOXY ESTERS AND INTERMEDIATES PREPARED THEREBY

FIELD OF THE INVENTION

This invention relates to chemical processes and novel chemical intermediates which are useful for preparing pharmaceutically important compounds.

BACKGROUND OF THE INVENTION

Compounds of the structural formula (I):

wherein
$R_1$ is $(L)_a—(CH_2)_b—(T)_c—Q$;
a is 0 or 1;
b is 3 to 14;
c is 0 or 1;
L and T are independently oxygen or $CH_2$;
Q is $C_{1-4}$alkyl, trifluoromethyl, furanyl, thienyl, cyclohexyl or phenyl, optionally monosubstituted with Br, Cl, $CF_3$, $C_{1-4}$alkoxy, or $C_{1-4}$alkyl;
$R_2$ and A are independently selected from H, $CF_3$, $C_{1-4}$alkyl, halogen or $NO_2$; or
$R_1$ is H and $R_2$ is $(L)_a—(CH_2)_b—(T)_c—Q$, wherein a, b, c, L, T and Q are as defined above; and
$R_5$ is lower alkyl,
are useful intermediates in the synthesis of pharmaceutically important compounds, for example, leukotriene antagonists. Such compounds are disclosed in copending applications, U.S. Ser. Nos. 07/195,355, 07/066,588 and 07/066,592. Leukotriene antagonists are useful pharmaceutical compounds which have been used to treat the symptoms of asthma and bronchospasm in mammals. An example of such an antagonist is the compound 2(S)-hydroxy-3(R)-[2-(carboxyethylthio)]-3-[2-(8-phenyloctyl)phenyl]propionic acid, which compound contains two chiral centers. As is often the case, optimal therapeutic activity is provided only by one configuration of the two chiral centers. It is therefore desirable to produce this material in a form which is highly enriched in only one absolute configuration of the chiral centers.

Current methods for preparing these pharmaceutical compounds proceed through the intermediacy of the racemic α-epoxy esters of formula (I). These compounds are produced via a Darzens condensation. Thus, substituted benzaldehydes of structural formula (V), wherein $R_1$, $R_2$ and A are as defined previously, are reacted with ethyl or methyl α-halo acetates to yield the desired α-epoxy esters. The substituted benzaldehydes are produced by methods common in the art, for example, Perchonock et al., *J. Med. Chem.*, 29, 1442-52 (1986); Perchonock et al., *J. Med. Chem.*, 28, 1145-47 (1985); and copending patent applications 07/195,355, 07/066,588 and 07/066,592, all of which are incorporated by reference.

The epoxy-esters produced in the Darzens condensation are reacted with a mercaptan, typically with a mercapto-alkyl or mercapto-aryl carboxylic acid ester to produce a hydroxy-sulfido ester. Upon hydrolysis of the diester, resolution of the enantiomers, via fractional crystallization of the salt formed with an optically active resolving agent, yields the optically pure leukotriene antagonist.

There are many methods for preparing α-epoxy esters of Formula (I). Among these well known methods are the Darzens condensation, alkaline peroxide oxidation of alkylidine malonic esters, peracid oxidation of α,β-unsaturated esters and alkaline closure of halohydrins See for example, House, H. O., *Modern Synthetic Reactions*, 292-329, 422-436, W. A. Benjamin, Inc., Philippines (1972). However, all of these methods yield a racemic epoxide product. There has been a report of a chiral Darzens condensation, Abdel-Magid et al., *Tet. Lett.*, 25, 3273-76 (1984), but it relies upon the use of expensive chiral auxillaries.

Methods for the production of non-racemic α-epoxy ketones are known. Annunziata et al., *Tet. Lett.*, 26, 2471-74 (1985), report a condensation of phenacyl halides with benzaldehydes in the presence of bovine serum albumin. Other methods generally consist of alkaline peroxide oxidation of the α,β unsaturated ketone in the presence of a chiral auxillary. In this regard, Marsman et al., *J. Org. Chem.*, 44, 2312(1970) have reported the use of benzyl quininium chloride; Banfi et al., *Synthetic Comm.*, 13, 12, 1049-52(1983) have reported the use of cyclodextrins; Colonna et al., *Tet. Lett.*, 27, 3, 387-90(1986) have reported the use of bovine serum albumin; and Julia et al., *Angew. Chem. Int. Ed. Engl.*, 19, 929-30(1980) have reported the use of polyamino acids. These procedures have had varying degrees of success, with perhaps the most promising stereochemical yields being obtained with oxidations in the presence of polyamino acids. Julia et al., *Annales de Oimica*, 79 102-4(1982) report chemical yields as high as 78-85% and enantiomeric excess (e.e.) of 78-93% for simple chalcones. However, these methods have proved ineffective for the substituted aryl products of this invention. In addition, the reaction conditions of Julia et al. require the use of either aromatic hydrocarbons or halocarbon solvents to obtain acceptable asymmetric induction in the product epoxide. In particular, hexane and cyclohexane are claimed to give very poor asymmetric induction. (See Julia et al., *J. Chem. Soc. Perkin Trans. I.* 1317-24(1982)). Aromatic hydrocarbon and halocarbon solvents are not favored for use in an industrial process due to their toxicity.

The conversion of a ketone to an ester has often been accomplished by the Baeyer-Villiger reaction. This involves the reaction of a ketone with a peracid followed by a rearrangement which inserts an oxygen between the carbonyl and one of the two substituents of the carbonyl. Electronic factors usually determine the relative ratio of the two possible products which may be obtained. However, since epoxides are well known to be acid labile, such a reaction has never been reported upon an aryl epoxy ketone.

Epoxy esters resulting from the Baeyer-Villiger reaction of a peracid with an α,β-unsaturated ketone have been reported in the chemical art. However, in most cases a complex mixture of products is obtained in which only a portion of the products contain an epoxide and the Baeyer-Villiger rearrangement inserts oxygen between either the carbonyl and epoxide or the carbonyl and the double bond. α-Epoxy esters are disfavored and formed in only minor amounts, if at all. (See DeBoer et al., *J. Org. Chem.*, 39, 1, 77–83(1974); Yokayama et al., *Bull. Chem. Soc. Japan*, 38, 9, 1498–1500(1965); Payne et al., *J. Org. Chem.*, 24, 284–6(1959); Walton et al., *J. Org. Chem.*, 22, 1161–5(1957)).

An unusual Baeyer-Villiger rearrangement has been reported to occur with hydrogen peroxide under alkaline conditions for certain 2-keto, Δ-3 A-nor-steroids (Levine et al., *J. Org. Chem.*, 31, 3189–92(1966) and Rucker, et al., *Arch. Pharm.*, 317, 561–4(1984)) to produce an α-epoxy lactone. This is in contrast to results obtained with oxidations of other substrates with peroxides under alkaline conditions, which results exclusively in epoxidation.

The α-epoxy ketones and α-epoxy esters of this invention are new. In addition, excepting certain chalcones substituted in the 2-position by a $C_{3-7}$alkoxy group, the α,β-unsaturated ketones of this invention, are also new. Examples of 2-alkoxy chalcones have been reported by Nagesam et al., *Acta Cienc Indica Ser. Chem.*, 10, 165–9 (1984), Profft et al., *J. Prakt. Chem.*, 19, 192–201 (1963) and Tsatsas et al., *Prakt. Akad. Athenon*, 35, 418–23 (1960).

SUMMARY OF THE INVENTION

The objects of this invention are to provide novel epoxy-ester intermediates and a process for preparing these novel intermediates which are useful in the preparation of pharmaceutical compounds.

In one aspect this invention comprises compounds according to formulae (II), (III) or (IV):

wherein
$R_1$ is $(L)_a$—$(CH_2)_b$—$(T)_c$—Q;
a is 0 or 1;
b is 3 to 14;
c is 0 or 1;
L and T are independently oxygen or $CH_2$;

Q is $C_{1-4}$alkyl, trifluoromethyl, furanyl, thienyl, cyclohexyl or phenyl, optionally monosubstituted with Br, Cl, $CF_3$, $C_{1-4}$alkoxy, or $C_{1-4}$ alkyl;

$R_2$ and A are independently selected from H, $CF_3$, $C_{1-4}$alkyl, halogen or $NO_2$; or $R_1$ is H and $R_2$ is $(L)_a$—$(CH_2)_b$—$(T)_c$—Q wherein a, b, c, L, T and B are as defined above; and $R_3$ may be phenyl, substituted phenyl, naphthyl or substituted naphthyl, where the substituents may be one or two halogen, $C_{1-4}$alkyl, $C_{1-4}$alkoxy or trifluoromethyl groups.

In another aspect, this invention is an improved method for the asymmetric epoxidation of α,β-unsaturated ketones of formula (II) which comprises reacting an α,β-unsaturated ketone with an oxidant, a base and a polyamino acid in a mixture of water and an aliphatic hydrocarbon solvent.

In still another aspect, this invention is a method for converting α-epoxy ketones of formula (III) into α-epoxy esters of formula (IV) which comprises treating the α-epoxy ketone with a peracid.

In a further aspect, this invention provides a method for the preparation of racemic or non-racemic epoxy esters which comprises (a) reacting an α,β-unsaturated ketone of formula (II) with an oxidant, a base and optionally a polyamino acid; and (b) reacting the resulting α-epoxy ketone with a peracid.

DETAILED DESCRIPTION OF THE INVENTION

An improved process for the asymmetric epoxidation of α,β-unsaturated ketones has been discovered. The improvement comprises conducting the epoxidation in a simple aliphatic hydrocarbon solvent, as described hereinafter, which improves the commercial utility of the process and results in high yields with excellent enantioselectivity. In addition, it has been shown that preequilibration of the unsaturated ketone with the polyamino acid prior to oxidation greatly enhances the rate of reaction. A new process for producing epoxy esters has also been invented. This process consists of treating an α-epoxy ketone with a peracid to effect the production of an epoxy ester in high yield. In a preferred embodiment, to produce the leukotriene antagonists mentioned hereinbefore, one may couple a process of producing a non-racemic α-epoxy ketone with the process of producing an α-epoxy ester to yield a two step process for producing the useful non-racemic epoxy ester intermediates of this invention.

The structure of the α,β-unsaturated ketone used in this process is given by structural Formula (II):

(II)

wherein
$R_1$ is $(L)_a-(CH_2)_b-(T)_c-Q$;
a is 0 or 1;
b is 3 to 14;
c is 0 or 1;
L and T are independently oxygen or $CH_2$;
Q is $C_{1-4}$alkyl, trifluoromethyl, furanyl, thienyl, or phenyl, optionally monosubstituted with Br, Cl, $CF_3$, $C_{1-4}$alkoxy, or $C_{1-4}$alkyl;
$R_2$ and A are independently selected from H, $CF_3$, $C_{1-4}$alkyl, halogen or $NO_2$; or
$R_1$ is H and $R_2$ is $(L)_a-(CH_2)_b-(T)_c-Q$, wherein a, b, c, L, T and Q are as defined above; and
$R_3$ is phenyl, substituted phenyl, naphthyl or substituted naphthyl, where the substituents may be one or two halogen, $C_{1-4}$alkyl, $C_{1-4}$alkoxy or trifluoromethyl groups.

The epoxidation is conducted by slurrying a polyamino acid with water in a hydrocarbon solvent optionally with a metal chelator, such as ethylenediaminetetraacetic acid (EDTA), admixing a base and adding the ketone substrate. The oxidant is then added slowly to this slurry. If necessary, additional base and oxidant may be added later in the reaction.

A polyamino acid is formed by the polymerization of the N-carboxy anhydride of one of the naturally occurring L-amino acids, or their corresponding D-enantiomers, as is well know in the art. However, not all polyamino acids are equally effective for inducing asymmetry in the product. Suitable polyamino acids are polyalanine, polyleucine and polyisoleucine. Polyleucine is particularly preferred. Suitable copolymers of these preferred amino acids may also be used. The number of residues in the polyamino acid is not critical, but polymers of molecular weights of about 500 to about 65,000 are preferred. Other optically active catalysts may be used, such as ephedrinium bromide, bovine serum albumin, cyclodextrin and benzylquininium chloride, but their asymmetric induction is usually less than that obtained with polyamino acids.

Figure 1:
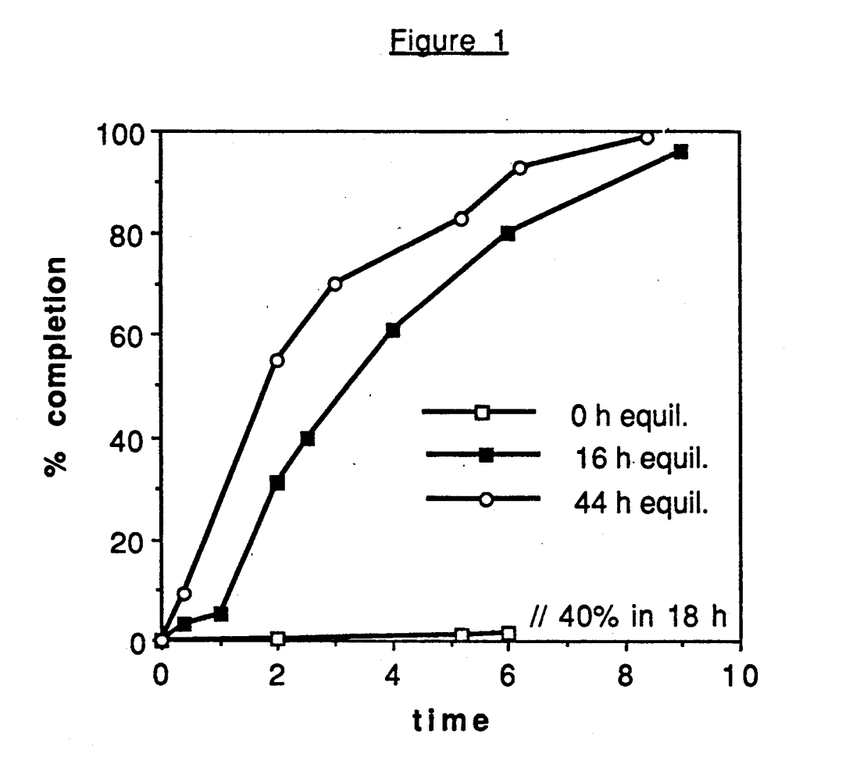
FIG. 1 demonstrates the effect of a preequilibration time on the rate of asymmetric epoxidation of (E)-1-(2-naphthalenyl)-3-[(2-(8-phenyloctyl)phenyl)]prop-2-ene-1-one. The substrate olefin was stirred with sodium hydroxide and poly-L-leucine in a mixture of water and n-hexane for 0 h, 16 h, or 44 h, as indicated, prior to the addition of hydrogen peroxide.

A particularly active form of the polyamino acid catalyst is prepared by "preswelling" the catalyst prior to the reaction. This is accomplished by stirring the catalyst in a mixture of water and the organic solvent in the presence of the base for from about 1 to about 72 hours. The substrate $\alpha,\beta$-unsaturated ketone may be added prior to the equilibration period or subsequent to the equilibration period, prior to addition of peroxide. This procedure effects an enhancement in the rate of epoxidation. A preequilibration time of 12-48 hours produces efficient results. A sample reaction profile depicting the effect of equilibration time on the rate of epoxidation is depicted in FIG. 1.

The polyamino acids used in this process may be recovered from the reaction mixture and subsequently recycled. Such "recovered" polymer will reproduce the same level or even higher levels of asymmetric induction as the original polymer. This is in contrast to previous reports in which lower levels of asymmetric induction were found. (Julia, S., et all, *Angew Chem. Int. Ed. Engl.*, 19, 929-930 (1980)).

The stereochemistry of the polyamino acid determines the stereochemistry of the resulting epoxide, and this appears to work complementarily. That is, if a poly-L-leucine produces one enantiomer, poly-D-leucine will produce the other. This process is particularly suited for the epoxidation of trans olefins. Epoxidation of cis olefins generally gives poor results.

For the purposes of the epoxidation, a two phase system of water and an organic solvent is preferred. Organic solvents include halocarbon solvents, aromatic and aliphatic hydrocarbon solvents, which are immiscible with water. Halocarbon solvents, such as carbon tetrachloride, methylene chloride, 1,2 dichloroethane, and aromatic hydrocarbon solvents, such as toluene, are useful in this reaction. Additionally, simple aliphatic hydrocarbon solvents, such as $C_{3-8}$ straight or branched chain alkanes or cycloalkanes, or 0 petroleum ethers, which have previously been claimed to be of little value due to their tendency to produce poor asymmetric induction, have been found to be particularly useful in this process. Aliphatic hydrocarbon solvents such as pentane, hexane, cyclohexane, heptane and petroleum ethers are suitable. Hexane is preferred.

Peroxides and peracids, such as hydrogen peroxide, alkyl hydroperoxides, such as t-butyl hydroperoxide, and inorganic oxidants, such as alkali metal hypochlorites and sodium peroxide are useful as oxidants in this process. Hydrogen peroxide is preferred.

Since oxidants such as hydrogen peroxide are generally somewhat unstable under the reaction conditions, long reaction times often require the addition of additional oxidant to replace that which naturally decomposes over time. It is useful, although not essential, to use metal chelators in the reaction mixture to bind any trace metals which may be present. Trace metals, such as iron, cause the decomposition of peroxide oxidants and thereby decrease the effective quantity of oxidant available to carry out the epoxidation reaction. Metal chelators such as organic polyamines inhibit this decomposition and are useful in this process in concentrations of about 0.01 to 5% wt/vol. Ethylenediaminetetraacetic acid (EDTA) is preferred.

Alkaline conditions are required to effect the epoxidation reaction. The base used to accomplish this may be an inorganic bicarbonate, carbonate or hydroxide; or an organic quaternary ammonium hydroxide, such as a tetra$C_{1-4}$alkyl ammonium hydroxide. Alkali metal hydroxides, such as lithium, sodium or potassium hydroxides, are favored. Sodium hydroxide is preferred.

Another aspect of this invention is the production of an $\alpha$-epoxy ester through the Baeyer-Villiger type rearrangement of an $\alpha$-epoxy ketone of structure (III):

(III)

wherein
$R_1$ is $(L)_a-(CH_2)_b-(T)_c-Q$;
a is 0 or 1;
b is 3 to 14;
c is 0 or 1;

L and T are independently oxygen or CH$_2$;

Q is C$_{1-4}$alkyl, trifluoromethyl, furanyl, thienyl, cyclohexyl or phenyl, optionally monosubstituted with Br, Cl, CF$_3$, C$_{1-4}$alkoxy, or C$_{1-4}$ alkyl;

R$_2$ and A are independently selected from H, CF$_3$, C$_{1-4}$alkyl, halogen or NO$_2$;

or R$_1$ is H and R$_2$ is (L)$_a$—(CH$_2$)$_b$—(T)$_c$—Q, wherein a, b, c, L, T and B are as defined above; and R$_3$ is phenyl or naphthyl unsubstituted or substituted by one or two halogen, C$_{1-4}$alkyl, C$_{1-4}$alkoxy or trifluoromethyl groups.

We now disclose a process for producing aryl epoxy esters by treating aryl epoxy ketones with a peracid. Typically the ketone is dissolved in a halocarbon or hydrocarbon solvent and treated with a peracid. Suitable solvents for this process are methylene chloride, 1,2 dichloroethane, carbon tetrachloride, chloroform, hexane and pentane. Methylene chloride and hexane are preferred. Peracids which are particularly useful in this process are perbenzoic acid and 3-chloroperbenzoic acid. 3-Chloroperbenzoic acid is preferred. In the case in which the α-epoxy ketone undergoing this process is optically active, the optical activity is preserved in the α-epoxy ester.

The choice of the R$_3$ group in the compounds used in this process may be a very practical one. Since, in most instances, R$_3$ will be removed at a later point, the choice of R$_3$ may be made based upon its price, availability and ease of use in preparing or isolating the α,β-unsaturated ketone or epoxy ketone or epoxy ester. It may also be chosen based upon its properties to confer crystallinity, solubility or reactivity to the intermediate epoxy ketone or subsequent epoxy ester. Such properties will aid in the ease of conducting the reaction, isolation of the products and purification of the products. In general, electron withdrawing substituents tend to favor more rapid reaction in the epoxidation process, while electron donating substituents facilitate the desired Baeyer-Villiger rearrangement.

A subset of substituents is most suitably employed in the overall two step process, which comprises (a) reacting an α,β-unsaturated ketone of formula (II) with an oxidant and a base and optionally a polyamino acid, and (b) reacting the resultant α-epoxy ketone with a peracid to form an α-epoxy ester of formula (IV). Phenyl, 4-bromophenyl, 4-methylphenyl, 4-fluorophenyl and naphthyl are preferred in this process for formation of a non-racemic α-epoxy ester. 2-Naphthyl is most favored due to its smooth epoxidation, its clean rearrangement in the Baeyer-Villiger reaction, and its tendency to confer crystallinity to the products. It will be appreciated by those skilled in the art that this two step process is useful for producing either a racemic or nonracemic ester depending upon the process used to produce the α-epoxy ketone. Accordingly, any method common to the art, which is useful for producing α-epoxy ketones from α,β-unsaturated ketones, is useful in this process. Methods common to this art are disclosed for instance in House, H. O., *Modern Synthetic Reactions*, 292–329, 422–436, W. A. Benjamin, Inc., Philippines (1972), and are incorporated 5 herein by reference. Stirring an α,β-unsaturated ketone in an alcoholic solvent such as methanol or ethanol, in the presence of hydrogen peroxide and a base, such as an alkali metal alkoxide, such as effectively sodium, potassium or lithium methoxide or ethoxide is a common example. They include, but are not limited to, epoxidation by stirring an α,β-unsaturated ketone in a suitable solvent in the presence of an oxidant and a base. The non-racemic epoxidation of this invention is another specific example of such processes, but is not intended to be a limitation upon this combination.

The non-racemic ester produced by this process is a most useful intermediate which can be used for the production of non-racemic α-epoxy amides, esters and acids. The epoxide moiety may also be further transformed by a nucleophilic addition to prepare non-racemic diols, non-racemic mercapto or thio alcohols or non-racemic amino alcohols; or the epoxide may be reduced to a non-racemic alcohol by methods common in the art. In all cases the optical activity is retained in the above transformations. See, for example J. M. Chong, et al., *J. Org. Chem.*, 50, 1560 (1965); K. Kato, et al., *J. Chem. Soc. Perkin I.* 1618 (1980); T. Hshiyama, *J. Chem. Soc. Perkin I*, 1725 (1984); J. Denis, et al., *J. Org. Chem.* 51, 46 (1986); Japanese Patent No. 61145159A, which are incorporated herein by reference. Such transformations and reductions are carried out according to methods well known to those skilled in the art.

This process of preparing non-racemic α-epoxy esters is particularly well suited to the preparation of leukotriene antagonists such as those disclosed in copending applications U.S. Ser. Nos. 07/195,355, 07/066,588 and 07/066,592. The present invention permits the production of the α-epoxy esters in the desired non-racemic form directly. These esters are then further converted into leukotriene antagonists by established methods, such as are disclosed by Gleason et al., *J. Med. Chem.*, 30, 959–61(1987). This invention thus results in the elimination of the resolution step required in earlier racemic processes and also results in a doubling of the efficiency of conversion of the substituted benzaldehyde to an α-epoxy ester, since very little of the undesired enantiomer is produced.

According to the process of the present invention, the substituted benzaldehyde (V) is converted to an α,β-unsaturated ketone of formula (II) by reaction with a substituted acetophenone or acetonaphthone using methods common in the art. The α,β-unsaturated ketone is reacted with a base, an oxidant and optionally, a metal chelator and a polyamino acid, to yield an α-epoxy ketone of formula (III), which is further reacted with a peracid to produce the α-epoxy ester of formula (IV). Accordingly, the intermediates (II), (III) and (IV), (II)

(III)

wherein
$R_1$ is $(L)_a$—$(CH_2)_b$—$(T)_c$—Q;
a is 0 or 1;
b is 3 to 14;
c is 0 or 1;
L and T are independently oxygen or $CH_2$;
Q is $C_{1-4}$alkyl, trifluoromethyl, furanyl, thienyl, cyclohexyl or phenyl, optionally monosubstituted with Br, Cl, $CF_3$, $C_{1-4}$alkoxy, or $C_{1-4}$ alkyl;
$R_2$ and A are independently selected from H, $CF_3$, $C_{1-4}$alkyl, halogen or $NO_2$;
or $R_1$ is H and $R_2$ is $(L)_a$—$(CH_2)_b$—$(T)_c$—Q, wherein a, b, c, L, T and Q are as defined above; and
$R_3$ is phenyl or naphthyl unsubstituted or substituted by one or two halogen, $C_{1-4}$alkyl, $C_{1-4}$alkoxy or trifluoromethyl groups, are useful and important intermediates for the production of pharmaceutical compounds by this process.

When the process of epoxidation in this invention is performed with a phase transfer catalyst, such as tetraalkyl ammonium chloride, and alkali metal hydroxide, without a polyamino acid, the resulting intermediate epoxyketone is racemic. If a poly-L-amino acid or poly-D-amino acid is used, a non-racemic epoxide is formed. Thus, both the racemates and the two non-racemic intermediates of formula (III) and (IV) are comprehended by this invention. In particular, compounds in which $R_1$ is undecyl, dodecyl, tridecyl, decyloxy, undecyloxy, dodecyloxy, phenylheptyl, phenyloctyl, or phenylnonyl are useful. The following compounds are especially preferred:

(E)-1-(2-naphthalenyl)-3-[2-(8-phenyloctyl)phenyl]-2-propen-1-one;
(E)-1-phenyl-3-[2-(8-phenyloctyl)phenyl]-2-propen-1-one;
(E)-1-(4-methylphenyl)-3-[2-(8-phenyloctyl)phenyl]-2-propen-1-one;
(E)-1-(4-fluorophenyl)-3-[2-(8-phenyloctyl)phenyl]-2-propen-1-one;
(E)-1-(2-naphthalenyl)-3-[2-(dodecyl)phenyl]-2-propen-1-one;
(E)-1-(2-naphthalenyl)-3-[2-(undecyloxy)phenyl]-2-propen-1-one;
(2R-trans)-(2-naphthalenyl) [3-[2-(8-phenyloctyl)phenyl]oxiranyl]methanone;
(2R-trans)-phenyl [3-[2-(8-phenyloctyl)phenyl]oxiranyl]methanone;
(2R-trans)-(4-methylphenyl) [3-[2-(8-phenyloctyl)phenyl]oxiranyl]methanone;
(2R-trans)-(4-bromophenyl) [3-[2-(8-phenyloctyl)phenyl]oxiranyl]methanone;
(2R-trans)-(4-fluorophenyl) [3-[2-(8-phenyloctyl)phenyl]oxiranyl]methanone;
(2R-trans)-(2-naphthalenyl) [3-[2-(dodecyl)phenyl]oxiranyl]methanone;
(2R-trans)-(2-naphthalenyl) [3-[2-(undecyloxy)phenyl]oxiranyl]methanone;
(2R-trans)-(2-naphthalenyl) 3-[2(8-phenyloctyl)phenyl]oxiranecarboxylate;
(2R-trans)-phenyl 3-[2-(8-phenyloctyl)phenyl]oxiranecarboxylate;
(2R-trans)-(4-methylphenyl) 3-[2-(8-phenyloctyl)phenyl]oxiranecarboxylate;
(2R-trans)-(4-bromophenyl) 3-[2-(8-phenyloctyl)phenyl]oxiranecarboxylate;
(2R-trans)-(4-fluorophenyl) 3-[2-(8-phenyloctyl)phenyl]oxiranecarboxylate;
(2R-trans)-(2-naphthalenyl) 3-[2-(dodecyl)phenyl]oxiranecarboxylate;
(2R-trans)-(2-naphthalenyl) 3-[2-(undecyloxy)phenyl]oxiranecarboxylate;and
(2R-trans)-phenyl 3-[2-(8-phenyloctyl)phenyl]oxiranecarboxylate.

α-Epoxyamides, which are produced by methods common to the art, are particularly useful derivatives of the compounds of formula (IV). Typically, stirring an α-epoxy ester of formula (IV) in a suitable solvent, such as an alcohol or acetone, with ammonium hydroxide, or saturating the solution with ammonia, produces the corresponding α-epoxyamide of formula (VI). Accordingly, the epoxyamides have the structure:

wherein
$R_1$ is $(L)_a$—$(CH_2)_b$—$(T)_c$—Q;
a is 0 or 1;
b is 3 to 14;
c is 0 or 1;
L and T are independently oxygen or $CH_2$;
Q is $C_{1-4}$alkyl, trifluoromethyl, furanyl, thienyl, cyclohexyl or phenyl, optionally monosubstituted with Br, Cl, $CF_3$, $C_{1-4}$alkoxy, or $C_{1-4}$alkyl;
$R_2$ and A are independently selected from H, $CF_3$, $C_{1-4}$alkyl, halogen or $NO_2$;
or $R_1$ is H and $R_2$ is $(L)_a$—$(CH_2)_b$—$(T)_c$—Q; wherein a, b, c, L, T and Q are as defined above. Suitably $R_1$ is phenylheptyl, phenyloctyl, phenylnonyl, undecyl, dodecyl, tridecyl, decyloxy, undecyloxy or dodecyloxy. Preferably A is H.

Such α-epoxyamides may be converted to leukotriene antagonists in the same manner as hereinbefore described, by treating the α-epoxyamide of formula (VI) with a suitable mercaptan, in the presence of a base, and subsequently hydrolyzing the carboxamide to an acid with aqueous or alcoholic acid. Mineral acids such as hydrochloric or sulfuric acid are preferred. Typically, an ester of formula (IV), such as (2R-trans)-2-naphthalenyl 3-[(2-(8-phenyloctyl)phenyl]oxiranecarboxylate, is treated with a solution of acetone and ammonium hydroxide at reflux to form the (2R-trans)-3-[(2-(8-phenyloctyl)phenyl]oxiranecarboxamide. Subsequent treatment with a mercaptan, such as methyl 3-mercaptopropionate, and a base, such as triethylamine, yields a mixture of the corresponding 2 -sulfido 3-hydroxy and the 3-sulfido 2-hydroxy carboxamides, which may be separated chromatographically. Hydrolysis of the 2(S)-hydroxy-3(R)-[2-(methylcarboxy)ethylthio]-3-[(2-(8-phenyloctyl)phenyl]oxiranecarboxamide with sodium hydroxide in a mixture of methanol and water, followed by acidic hydrolysis using 6 N HCl yields the compound 2(S)-hydroxy-3(R)-[2-(carboxyethylthio)]-3-[2-(8-phenyloctyl)phenyl]propionic acid. (2R-trans)-3-[2-(8-phenyloctyl)phenyl]oxiranecarboxamide is a preferred intermediate compound.

The following examples are intended in no way to limit the scope of this invention, but are provided to illustrate the use of this invention. The nomenclature and abbreviations common to the chemical art are used in the examples. Melting points are uncorrected. Liquid chromatography was conducted on a Baker Chiralpak OP (+) chiral HPLC column (25 cm×4.6 mm) or Waters C-18 μ-Bondapak® (30 cm×3.9 mm), using the specified solvent and flow rate. Thin-layer chromatographic analyses were carried out on Analtech silica gel GF (250 μm) plates using the specified solvent as eluent; visualization was effected by either ultraviolet light or by charring with phosphomolybdic acid and 50% sulfuric acid. The polyleucine and polyalanine may be purchased from Sigma Chemical Co., St. Louis, Mo., or may be prepared by the methods of this invention. Unless otherwise indicated all $^{13}$C-NMR (carbon magnetic resonance) were obtained at 90 MHz and $^{1}$H-NMR (proton magnetic resonance) spectra were obtained at 360.13 MHz, using a Bruker Instruments WM360 spectrometer in deuterochloroform solution. $^{13}$C spectra were run using the GASPE (Gated-SpinEcho) pulse sequence. Annotations to $^{1}$H-NMR are as follows: s, singlet; d, doublet; t, triplet; br, broad; m, multiplet; J, coupling constant in Hertz. Optical purity of the epoxy esters and epoxy ketones was determined by $^{1}$H NMR in deuterochlorform using 5-20 equivalents of the chiral shift reagent (S)-(+)-2,2,2-trifluoro-1-(9-anthryl)ethanol. The integration of the chiral oxirane protons was used to ascertain the enantiomeric purity.

EXAMPLE 1 a) Preparation of (2R-trans)-phenyl 3-[2-(8-phenyloctyl)phenyl]oxiranecarboxylate a) Preparation of (E)-1-phenyl-3-[2-(8-phenyloctyl)-phenyl]-2-propen-1-one.

To a cooled solution of absolute ethanol (105 mL) in a 250 mL roundbottom flask equipped with overhead stirring and an ice bath, was added small pieces of sodium metal (1.04 g, 0.06 mol). After the sodium had dissolved the cooling bath was removed and the reaction was stirred at 25° C. Acetophenone (2.44 g, 0.02 mol) and 2-(8-phenyloctyl) benzaldehyde (6.0 g, 0.020 mol) were successively added. After 2.5 h the reaction was complete as ascertained by TLC (CH$_2$Cl$_2$:n-hexane, 3:1; Silica gel GF). The reaction was concentrated at reduced pressure, treated with water (50 mL), and the product extracted into diethyl ether. The combined ether layers were washed with water and dried over MgSO$_4$, and the solvent was evaporated. The crude product (8 g) was dissolved in methylene chloride:n-hexane (3:1) and purified by flash chromatography over silica gel (320 g), eluting with the same solvent mixture. The appropriate fractions were combined to yield the propenone (4.24 g, 53.5%) as an oil. IR (thin film) 2924, 2858, 1660, 1590-1600 (s), 1330, 1210 (s) cm$^{-1}$; $^{1}$H NMR (CDCl$_3$, 360 MHz) δ 8.14 (d, 1 H, olefinic proton, J=15.6 Hz), 7.50 (d, 2 H, J=15.6 Hz, olefinic proton), 7.12-8.04 (m, 14 H), 2.77 (t, 2 H, J=7.7 Hz, ArCH$_2$), 2.58 (t, 2 H, J=7.7 Hz, ArCH$_2$), 1.56 (m, 4 H), 1.29 (b, 8 H); $^{13}$C NMR (CDCl$_3$) δ 190.53, 143.32, 142.92, 142.52, 138.31, 133.43, 132.71, 130.23, 130.17, 128.60, 128.52, 128.39, 128.20, 126.55, 126.31, 125.53, 123.34, 35.94, 33.40, 31.73, 31.44, 29.40, 29.26; TLC R$_f$ 0.50 (CH$_2$Cl$_2$:n-hexane, 3:1, Silica gel GF); HPLC RT 17.7 min (Waters μ-Bondapak® C-18; 30 cm×3.9 mm; CH$_3$CN:water, 85:15; 1.5 mL/min; UV detection at 230 nm). Anal. Calcd for C$_{29}$H$_{32}$O: C, 87.84; H, 8.08. Found: C, 87.53; H, 8.07.

b) Preparation of (2R-trans)-phenyl [3-[2-(8-phenyloctyl)phenyl]oxiranyl]methanone.

(E)-1-phenyl-3-[2-(8-phenyloctyl)phenyl]-2-propen-1-one (0.123 g, 0.315 mmol) was dissolved in toluene (1.1 mL) with poly-L-alanine (0.07 g) and a cooled solution of sodium hydroxide (0.120 g, 3 mmol) in hydrogen peroxide (H$_2$O$_2$ 30% in water, 1.5 mL) was added. After stirring 20 h at ambient temperature, additional sodium hydroxide (0.08 g) in hydrogen peroxide (1.0 mL) was added and the reaction stirred for an additional 24 h. The reaction was filtered and the filter cake (mainly polymer) was washed with toluene. The filtrate was evaporated to yield an oil (0.12 g) which was purified by chromatography on silica gel (6 g) eluting with methylene chloride:n-hexane 1:3, followed by a 1:1 methylene chloride:n-hexane. The product was an amber oil. $^{1}$H-NMR mixture. The product was an amber oil. $^{1}$H-NMR (CDCl$_3$, 360 MHz, 15 equivalents of (S)-(+)-2,2,2-trifluoro-1-(9-anthryl)ethanol as chiral shift reagent) gave 80% e.e. by examination of the peak intensities of the oxirane methine protons. CD:[θ]$_{327}$ −10,250 (c 0.1 mg/mL, CH$_3$CN); IR (thin film) 2930 (s), 2855, 1690 (s), 1600, 1503, 1405, 1230 (s), 1004, 890 (br) cm$^{-1}$; $^{1}$H NMR (CDCl$_3$, 360 MHz) δ 1.11-1.32 (m, 8 H), 1.52 (m, 4 H), 2.57 (t, 2 H, J=7.7 Hz), 2.64-2.71 (m, 2 H), 4.23 (d, 1 H, J=1.8 Hz, oxirane proton), 4.27 (d, 1 H, J=1.8 Hz, oxirane proton), 7.16-7.62 (m, 12 H), 8.03 and 8.04 (d, 2 H); TLC R$_f$ 0.41 (CH$_2$Cl$_2$, Silica gel GF); HPLC RT 9.79 min (OP(+); 25 cm×4.6 mm; CH$_3$OH; 1 mL/min; UV detection at 230 nm, no separation of enantiomers); mass spectrum CI/CH$_4$ m/e 413 (M+H)$^+$; CI/NH$_3$ 430 (M+NH$_4$)$^+$. Anal. Calcd for C$_{29}$H$_{32}$O$_2$: C, 84.42; H, 7.81. Found: C, 83.26; H, 7.75.

c) Preparation of (2R-trans)-phenyl 3-[2-(8-phenyloctyl)phenyl]oxiranecarboxylate.

The oxiranylmethanone (80% e.e., 0.35 g, 0.85 mmol) of Example 1b and methylene chloride (10 mL) in a roundbottom flask (25 mL) equipped with a magnetic stirrer was treated with 3-chloroperbenzoic acid (85%, 0.35 g, 1.73 mmol). The solution was stirred at reflux for 15 h at which time the reaction was shown to be complete by TLC. The solution was cooled to 10° C., and the precipitated 3-chlorobenzoic acid was removed by chromatography on silica gel (20 g) and the product eluted with CH$_2$Cl$_2$:n-hexane, 3:1. The product was obtained as an oil in 45% yield. $^{1}$H-NMR (CDCl$_3$, 360 MHZ, 9 equivalents of (S)-(+)-2,2,2-trifluoro-1-(9-anthryl)ethanol as chiral shift reagent) gave 81.6% e.e. by examination of the peak intensities of the oxirane methine protons.

CD:[θ]$_{231}$ −20,400 (c 0.1 mg/mL, CH$_3$CN); $^{1}$H NMR (CDCl$_3$, 360 MHz) δ 1.32 (br, 8 H), 1.61 (m, 4 H), 2.56 (t, 2 H, J=8 Hz), 2.74 (m, 2 H), 3.64 (d, 1 H, J=1.7 Hz, oxirane proton), 4.43 (d, 1 H, J=1.5 Hz, oxirane proton), 7.16-7.69 (m, 14 H); $^{13}$C NMR (CDCl$_3$) δ 166.89, 151.40, 142.40, 141.38, 132.59, 129.57, 129.36, 128.66, 128.36, 128.20, 126.36, 126.31, 125.53, 124.39, 121.13, 56.49, 56.16, 35.91, 32.84, 31.39, 31.14, 29.55, 29.43, 29.34, 29.23; TLC R$_f$ 0.61 (CH$_2$Cl$_2$, Silica gel GF), 0.56 (CH$_2$Cl$_2$:n-hexane, 3:1); mass spectrum CI/NH$_3$ m/e 446 (M+NH$_4$)$^+$. Anal. Calcd for C$_{29}$H$_{32}$O$_3$: C, 81.27; H, 7.53. Found: C, 83.92; H, 7.80.

EXAMPLE 2

Preparation of (2R-trans)-(4-fluorophenyl) 3-[2-(8-phenyloctyl)phenyl]oxiranecarboxylate a) Preparation of (E)-1-(4-fluorophenyl)-3-[2-(8-phenyloctyl)phenyl]-2-propen-1-one.

To a cooled solution of ethanol (95%, 89 mL) in a 250 mL roundbottom flask equipped with overhead stirring was added small pieces of sodium metal (0.937 g, 40.8 mmol). After the sodium had dissolved the cooling bath was removed and the reaction temperature was 24° C. The solution was treated with 4-fluoroacetophenone (2.34 g, 17.0 mmol) and 2-(8-phenyloctyl)benzaldehyde (5.0 g, 17.0 mmol) at such a rate that the temperature did not exceed 28° C. The yellow solution was stirred for 3 h at ambient temperature. The reaction was concentrated in vacuo to an oil. The crude product was dissolved in diethyl ether and washed with water (100 mL). The ether layer was dried (MgSO$_4$) and evaporated under reduced pressure to afford an oil. The oil was placed in a vacuum desiccator at 0.2 mm Hg for 19 h, yielding the unsaturated ketone as a pale oil, 6.62 g (94%). IR (thin film) 3080, 3040, 2940, 2860, 1670, 1600 (s), 1360, 1235, 1215 cm$^{-1}$; TLC R$_f$ 0.53 (CH$_2$Cl$_2$:hexane, 3:1, Silica gel GF); HPLC RT 10.62 min (OP(+); 25 cm×4.6 mm; CH$_3$OH; 0.8 mL/min; UV detection at 230 nm).

b) Preparation of (2R-trans)-(4-fluorophenyl) [3-[2-(8-phenyloctyl)phenyl]oxiranyl]methanone.

Sodium hydroxide pellets (5.4 g, 135 mmol) and hydrogen peroxide (H$_2$O$_2$ 30% in water, 72 mL, 698 mmol) were cooled to 0° C. in a magnetically stirred 200 mL roundbottom flask. After 0.5 h, the sodium hydroxide had dissolved, and n-hexane (56 mL) and poly-L-leucine (Sigma, 3.78 g) were added. After 15 min the compound of Example 2a (purity 92%, 4.5 g, 9.97 mmol) was added and the reaction stirred at ambient temperature for 22 h. The poly-L-leucine was filtered and washed with hot ether and saturated sodium chloride. The layers were separated and the organic layer washed with brine, dried (MgSO$_4$), filtered, and evaporated to a semisolid. The crude oxiranylmethanone was dissolved in boiling n-hexane (about 60 mL) and placed in the refrigerator for 20 h. The resulting white crystals were collected and dried at 1 mm Hg, yielding 3.0 g (69%) of the desired product. The product was >98% e.e. as determined by HPLC. Mp 53°-54° C.; $^1$H NMR (CDCl$_3$, 360 MHz) δ 1.21 (b, 8 H), 1.53 (b, 4 H), 2.57 (t, 2 H, J=8.0 Hz), 2.65 (m, 2 H), 4.14 (d, 1 H, J=2.04 Hz, oxirane proton), 4.25 (d, 1H, J=1.81 Hz, oxirane proton), 7.13-7.34 (m, 11 H), 8.08 (m, 2 H, coupled to F); TLC R$_f$ 0.29 (CH$_2$Cl$_2$:n-hexane, 3:1, Silica gel GF); HPLC RT 9.2 min (2R-enantiomer), 12.25 min (2S-enantiomer) (OP(+); 25 cm×4.6 mm; CH$_3$OH; 0.8 mL/min; UV detection at 230 nm).

Anal. Calcd for C$_{29}$H$_{31}$OF: C, 80.90; H, 7.26; F, 4.41. Found: C, 80.72; H, 7.28; F, 4.42.

c) Preparation of (2R-trans)-(4-fluorophenyl) 3-[2-(8-phenyloctyl)phenyl]oxiranecarboxylate.

The oxiranylmethanone (1.5 g, 3.47 mmol) of Example 2b was dissolved in 1,2-dichloroethane (30 mL) and treated with 3-chloroperbenzoic acid (85%, 1.6 g, 90 mmol) and 2,6-di-t-butyl-4-methylphenol (3 mg, stabilizer for 3-chloroperbenzoic acid). The solution was stirred at reflux for 16 h. The reaction was cooled (5° C.), and the precipitated 3-chlorobenzoic acid was removed by filtration, and washed with 1,2-dichloroethane (10 ml). Ice water (50 mL) containing sodium thiosulfate (0.5 g) was added and the layers were separated. The aqueous layer was washed with methylene chloride and the combined organic layers were washed with dilute aqueous potassium bicarbonate (2%), water, and brine. The solution was evaporated to give a yellow oil which did not solidify on standing. The oil was kept under reduced pressure (0.5 mm Hg) to constant weight (1.4 g); HPLC purity by peak area, 87%. The proton NMR indicated the presence (δ 8.16, 8.23) of 10-15% of an impurity assigned as 1-[2-(8phenyloctyl)phenyl]-1-formate-1-(4-fluorobenzoate)methane. For the desired product: $^1$H NMR (CDCl$_3$, 360 MHz) δ 3.63 (d, 1 H, J=1.8 Hz, oxirane proton), 4.42 (d, 1 H, J=1.8 Hz, oxirane proton); TLC R$_f$ 0.39 (CH$_2$Cl$_2$:n-hexane, 3:1, Silica gel GF); HPLC RT 7.48 min, peak area 87.4%, (Rainin ODS column; 25 cm×4.6 mm; CH$_3$CN:Water:Acetic Acid, 90:10:1; 2 mL/min; UV detection at 230 nm).

EXAMPLE 3

Preparation of (2R-trans)-(4-brommophenyl) 3-[2-(8-phenyloctyl)phenyl]oxiranecarboxylate a) Preparation of (E)-1-(4-bromophenyl)-3-[2-(8-phenyloctyl)phenyl]-2-propen-1-one.

The α,β-unsaturated ketone was prepared from 4-bromoacetophenone (33.8 g, 0.169 mol), 2-(8-phenyloctyl)benzaldehyde (50.0 g, 0.170 mol), and sodium (9.12 g, 0.39 mol) in ethanol (95%, 875 mL) by the procedure of Example 1a. The yield after distillation was 66.36 g (82%). Bp 238-240° C. (0.025 mm Hg); IR (thin film) 2905, 2855, 1710 (br), 1580-1600 (s), 1455, 1400, 1320(b), 1210, 1180, 1009 cm$^{-1}$; $^1$H NMR (CDCl$_3$) δ 1.28-1.44 (8 H), 1.56 (4 H), 2 56 (t, 2 H, J=7.7 Hz, ArCH$_2$), 2.75 (t, 2 H, J=7.8 Hz, ArCH$_2$), 7.13-7.69 (m, 9 H), 7.38 (d, 1 H, J=15.5 Hz, olefinic proton) 7.62, (d, 2 H, J=8.5 Hz), 7.87 (d, 2 H, J=8.5 Hz), 8.13 (d, 1 H, J=15.5 Hz, olefinic proton); $^{13}$C NMR (CDCl$_3$), δ 188.99, 143.31, 142.81, 142.72, 136.87, 133.06, 131.77, 130.34, 130.09, 129.91, 128.26, 128.09, 127.71, 126.43, 126.25, 125.43, 122.43, 35.86, 33.27, 31.66, 31.35, 29.31, 29.26, 29.17; TLC R$_f$ 0.57 (CH$_2$Cl$_2$:n-hexane, 3:1, Silica gel GF); HPLC RT 14.3 min (OP(+); 25 cm×4.6 mm; CH$_3$OH; 1 ml/min; UV detection at 230 nm), RT 8.21 min (Waters μ-PORASIL; 30 cm×3.9 mm; n-hexane:isopropanol, 90:10; 0.8 mL/min; UV detection at 231 nm); mass spectrum (CI/methane) m/e 475 (M)$^+$, Anal. Calcd for C$_{29}$H$_{31}$OBr: C, 73.36; H, 6.57; Br, 16.80. Found: C, 73.36; H, 6.70; Br, 17.28.

b) Preparation of (2R-trans)-(4-bromophenyl) [3-[2-(8-phenyloctyl)phenyl]oxiranyl]methanone.

A suspension Of poly-L-leucine (0.45 g) in n-hexane (8 mL) was stirred magnetically at 15° C. for 0.5 h, and treated with a cooled solution of NaOH (0.64 g, 16 mmol) in hydrogen peroxide (H$_2$O$_2$ 30% in water, 8.4 mL). The solution was cooled to 10°-15° C. for 10 min and then the chalcone from Example 3a (0.60 g, 1.26 mmol) was added. The reaction was monitored by TLC (CH$_2$Cl$_2$:n-hexane, 3:1; Silica gel GF; charring with phosphomolybdic acid and 50% sulfuric acid). After 17 h the reaction was nearly complete. The thick reaction was filtered and the flask rinsed with hot toluene. The collected poly-L-leucine was washed free of product with hot n-hexane and brine, and the organic layer separated and washed with brine. Evaporation yielded a thick oil which slowly solidified. Chiral HPLC showed the product at >98% e.e. (OP(+); 25 cm×4.6 mm; CH$_3$OH; 0.8 mL/min; UV detection at 231 nm).

Alternate preparation of (2R-trans)-(4-bromophenyl) [3-[2-(8-phenyloctyl)phenyl]oxiranyl]methanone A solution of the chalcone from Example 3a (40.5 g, 0.085 mol) in CCl$_4$ (400 mL) was stirred with efficient overhead stirring at room temperature for 5 min, and the solution treated with poly-L-leucine (32 g) and the mixture stirred at 25° C. for 1 h. The reaction was cooled to 5-9° C. and then treated with a solution of NaOH (45.0 g, 1.12 mol) in hydrogen peroxide (H$_2$O$_2$ 30% in water, 500 mL, 2.27 mol) cooled to 5° C., and water (50 mL). The reaction was cooled periodically to prevent any foaming. The reaction was stirred at ambient temperature for 16 h, filtered and washed with hot methylene chloride (400 mL) and water. The reaction was transferred to a separatory funnel and the layers separated. The aqueous layer was washed with methylene chloride, and the combined organic layers washed with brine, and dried (MgSO$_4$). The resulting semi-solid (37 g) was dissolved in boiling n-hexane (ca. 350 mL) and placed in the refrigerator for 16 h. Filtration of the hexane solution yielded 31.7 g (76%) of the desired oxiranylmethanone, which assayed at >96.9% e.e. via HPLC Mp 57°-58° C.; $[\alpha]_D$ −36.2° (c 1.0, EtOH, 25° C.), $[\alpha]_{546}$ −49.6°; IR (nujol) 1689, 1590, 1420, 1240, 1074, 1015, 900, 760 cm$^{-1}$; $^1$H NMR (CDCl$_3$, 360 MHz) δ 1.14-1.28 (m, 8 H), 1.48-1.59 (m, 4 H), 2.59 (t, 2 H) 2.65 (m, 2 H), 4.15 (d, 1 H, J=1.83 Hz, oxirane proton), 4.26 (d, 1 H, J=1.76 Hz, oxirane proton), 7.17-7.35 (m, 9 H), 7.64 (d, 2 H, J=8.52 Hz), 7.92 (d, 2 H, J=8.52 Hz); $^{13}$C NMR (CDCl$_3$) δ 192.36, 142.79, 141.33, 134.13, 133.11, 132.22, 129.82, 129.34, 128.58, 128.36, 128.18, 126.42, 125.53, 124.14, 60.40, 57.54, 35.89, 32.68, 31.33, 31.17, 29.38, 29.27, 29.18; TLC R$_f$ 0.41 (CH$_2$Cl$_2$:n-hexane, 3:1, Silica gel GF); HPLC RT 11.9 min, 18.5 min for (2S-enantiomer) (OP(+); 25 cm×4.6 mm; CH$_3$OH; 0.8 mL/min; UV detection at 230 nm). Anal. Calcd for C$_{29}$H$_{31}$BrO: C, 70.87; H, 6.35; Br, 16.25. Found: C, 70.45; H, 6.41; Br, 16.15.

c) Preparation of (2R-trans)-(4-bromophenyl) 3-[2-(8-phenyloctyl)phenyl]oxiranecarboxylate.

The above oxiranylmethanone from Example 3b (2.0 g, 4.05 mmol) in methylene chloride (22 mL) was treated with 3-chloroperbenzoic acid (85%, 2.0 g, 9.86 mmol), and the reaction stirred at reflux for 16 h. TLC showed only a trace of the starting material remaining. The reaction was cooled to 10° C., and the precipitated 3-chlorobenzoic acid removed by filtration. The precipitate was washed with cold methylene chloride, and the combined organic layers evaporated on the rotary evaporator. HPLC (Spherisorb ® see below) indicated the presence of 5% (peak area) of an impurity identified as 1-[2-(8-phenyloctyl)phenyl]-1-formate-1-(4-bromobenzoate)methane. The desired product was isolated in a pure form by dissolving the product in boiling isopropanol, and allowing the solution to stand at 5° C. for 16 h. The crystalline product was filtered and washed with a small volume of cold isopropanol and dried at 30° C. in vacuo to yield the oxiranecarboxylate 1.2 g (58%) optically pure via chiral HPLC; mp 53°-56° C.; $[\alpha]_D$ −54.4° (c 1.0, EtOH); IR (nujol) 1768 (s), 1480, 1343, 1240, 1175, 1070, 1018, 850 cm$^{-1}$. $^1$H NMR (CDCl$_3$, 360 MHz) δ 1.30 (br, 8 H), 1.64 (m, 4 H), 2.58 (t, 2 H, J=7.7 Hz), 2.75 (m, 2 H), 3.61 (d, 1 H, J=1.71 Hz, oxirane proton), 4.40 (d, 1 H, J=1.71 Hz, oxirane proton), 7.08-7.33 (m, 9 H), 7.06 (d, 2 H, J=8.92 Hz), 7.52 (d, 2 H, J=8.96 Hz); $^{13}$C NMR (CDCl$_3$) δ 166.57, 149.29, 142.76, 141.36, 132.62, 132.38, 129.38, 128.73, 128.34, 126.39, 125.56, 124.37, 122.89, 119.46, 56.58, 56.00, 35.90, 32.81, 31.38, 31.11, 29.52, 29.41, 29.23; TLC R$_f$ 0.66 (CH$_2$Cl$_2$:hexane, 3:1, Silica gel GF), R$_f$ 0.60 (CHCl$_3$); HPLC RT 16.64 min (Spherisorb ® Silica; 25 cm×4.6 mm; hexane:isopropanol, 9:1, 0.8 mL/min; UV detection at 230 nm).

Anal. Calcd for C$_{29}$H$_{31}$BrO$_2$: C, 68.64; H, 6.16; Br, 15.74. Found: C, 68.24; H, 6.18; Br, 15.68.

EXAMPLE 4

Preparation of (2R-trans)-(4-methylphenyl) 3-[2-(8-phenyloctyl)phenyl]oxiranecarboxylate a) Preparation of (E)-1-(4-methylphenyl)-3-[2-(8-phenyloctyl)phenyl]-2-propen-1-one.

To a cooled solution of absolute ethanol (325 mL) was added sodium (5.4 g, 0.225 mol) and the reaction stirred for 30 min, and then 4-methyl acetophenone (7.35 g, 54.8 mmol) in absolute ethanol (100 mL) and 2-(8-phenyloctyl)benzaldehyde (16.14 g, 54.8 mmol) were added. After 18 h the reaction was treated with concentrated HCl (20 mL), water (150 mL) and extracted with methylene chloride (2×600 mL). The combined extracts were dried (MgSO$_4$), filtered, and concentrated to afford a yellow oil. The oil was distilled (Kugelrohr, 220°-225° C., 0.005 mm Hg) to afford 18.3 g (81%) of the chalcone as a yellow oil. $^1$H NMR (CDCl$_3$, 360 MHz) δ 1.41 (br, 8 H), 1.69 (br, 4 H), 2.49 (s, 3 H, ArCH$_3$), 2.68 (t, 2 H, J=7.7 Hz), 2.87 (t, 2 H, J=7.7 Hz), 7.23-7.44 (m, 9H), 7.56 (d, 1 H, J=15.5 Hz, olefinic proton), 7.79 (d, 1 H), 8.05 (d, 2 H, J=8.07 Hz), 8.27 (d, 1 H, J=15.5 Hz); $^{13}$C NMR (CDCl$_3$) δ 189.56, 143.32, 143.03, 142.68, 141.78, 135.56, 133.35, 129.96, 129.15, 128.50, 128.22, 128.04, 126.39, 126.15, 125 37, 123.06, 35.81, 33.23, 31.57, 31.30, 29.28, 29.12, 21.47 (ArCH$_3$); mass spectrum CI/CH$_4$ m/e 411 (M+H)$^+$.

Anal. Calcd for C$_{30}$H$_{34}$O: C, 87.76; H, 8.35. Found: C, 87.86; H, 8.27.

b) Preparation of (2R-trans)-(4-methylphenyl) [3-[2-(8-phenyloctyl)phenyl]oxiranyl]methanone.

To a stirred mixture of poly-L-leucine (120 g), n-hexane (1770 mL), and hydrogen peroxide (H$_2$O$_2$ 30% in water, 2000 mL) at 15° C. was added a solution of NaOH (183 g, 4.575 mol) in water (300 mL) over 30 min. The reaction was stirred and maintained at <35° C. with an ice bath for 2 h. The propen-1-one of Example 4a (147.48 g, 0.359 mol) in n-hexane (300 mL) was added over 10 min at 30° C. The yellow mixture was stirred at 25° C. After 18 h, additional hydrogen peroxide (500 ml) was added and the temperature, which rose to 35° C., was brought to 25° C. with an ice bath. After a total of 42 h, the reaction was filtered and the insoluble polymer was washed with hot hexane (600 mL). The combined organic layers were collected and washed with brine, dried (MgSO$_4$), and evaporated to leave an orange oil. This material was of sufficient purity to use in the subsequent oxidation step, Example 4c. $^1$H NMR (CDCl$_3$, 400 MHz, Bruker) δ 7.95 (d, 2 H), 7.1-7.4 (m, 11 H), 4.22 (d, 1 H, J=1.5 Hz, oxirane proton), 4.18 (d, 1 H, J=1.5 Hz, oxirane proton), 2.58-2.65 (m, 2 H), 2.54-2.57 (m, 2 H), 2.38 (s, 3 H), 1.40-1.55 (m, 4 H), 1.02-1.29 (m, 8 H); HPLC RT 10.9 min (Waters μ-Bondapak ®; 30 cm×3.9 mm; CH$_3$CN:water, 7:3; 2 mL/min; UV detection at 230 nm).

c) Preparation of (2R-trans)-(4-methylphenyl) 3-[2-(8-phenyloctyl)phenyl]oxiranecarboxylate.

The oxiranylmethanone (144.63 g, 0.34 mol) of Example 4b in n-hexane (6 L, Baker) in a 12 L flask equipped with overhead stirring and heating mantle was treated with 3-chloroperbenzoic acid (85%, 64.23 g, 0.316 mol). The solution was refluxed for 4 h, additional 3-chloroperbenzoic acid (18.0 g, 0.09 mol) was added and the reaction refluxed 16 h. The reaction was cooled to 10° C., and the 3-chlorobenzoic acid by-product removed by filtration. The organic layer was washed with saturated sodium bicarbonate (2×lL), dried (MgSO$_4$), and evaporated to afford a yellow oil. Crystallization from n-hexane gave the epoxy ester as a pale yellow solid, 103.1 g (69%). Mp 38°-39° C.; $^1$H NMR (CDCl$_3$, 400 MHz, Bruker) δ 7.0-7.3 (m, 11 H), 7.03 (d, 2 H, J=8.48 Hz), 4.40 (d, 1 H, J=1.60 Hz, oxirane proton), 3.60 (d, 1 H, J=1.70 Hz, oxirane proton), 2.67-2.78 (m, 2 H), 2.56 (t, 2 H, J=7.6 Hz), 1.61 (m, 4 H), 1.29 (br, 8 H).

EXAMPLE 5

Preparation of (2R-trans)-(2-naphthalenyl) 3-[2-(8-phenyloctyl)phenyl)phenyl]oxiranecarboxylate a) Preparation of (E)-1-(2-naphthalenyl)-3-[2-(8-phenyloctyl)phenyl]-2-propen-1-one.

To a cooled (5° C.) solution of ethanol (95%, 3.53 L) in a 12 L 3-neck flask, under nitrogen, was added sodium metal (36.8 g, 1.16 mol) over a period of 30 min. After the sodium had dissolved, stirring was continued for 5 min, and 2-(8-phenyloctyl)benzaldehyde (200 g, 0.68 mol) was added. The reaction was cooled to 10° C. and 2-acetonaphthone (115.6 g, 0.679 mol) was added in one portion. The reaction was seeded with the desired product (2 g) and stirred for 18 h at ambient temperature. A yellow precipitate was present after that time. The reaction was treated with ice water (350 mL), cooled to 10° C., and filtered. The filter cake was washed with 50% aqueous ethanol (400 mL). The product, a yellow solid, was air dried and any lumps were pulverized. The product was dried at 25° C. (0.1 mm Hg) for 24 h to yield 248 g (89%): mp 41.0-42.5° C.; IR (KBr) 1658, 1597, 1467, 1325, 1185, 1124, 1016, 970, 763 cm$^{-1}$; $^1$H NMR (CDCl$_3$, 360 MHz) δ 8.55 (d, 1 H, naphthyl-1H, J=1.2 Hz), 8.21 (d, 1 H, J=15.5 Hz, olefinic proton), 7.12-8.11 (m, 15 H), 7.62 (d, 1 H, J=15.6 Hz), 2.75 (t, 2 H, J=7.71 Hz), 2.57 (t, 2 H, J=7.71 Hz), 1.59 (b, 4 H), 1.29 (b, 8 H); 13C NMR (CDCl$_3$) δ 190.25, 143.31, 142.86, 142.40, 135.59, 135.46, 133.47, 132.57, 130.21, 130.15, 129.91, 129.47, 128.52, 128.34, 128.15, 127.79, 126.72, 126.58, 126.31, 125.47, 124.49, 123.34, 35.91, 33.39, 31.72, 31.42, 29.41, 29.38, 29.34, 29.23; TLC R$_f$ 0.55 (CH$_2$Cl$_2$:n-hexane, 3:1, Silica gel GF); HPLC RT 17.7 min (Waters μ-Bondapak ® C-18; 30 cm×3.9 mm; CH$_3$CN:water, 85:15; 1.5 ml/min; UV detection at 230 nm). Anal. Calcd for C$_{33}$H$_{34}$O: C, 88.74; H, 7.67. Found: C, 88.84; H, 7.68.

b) Preparation of (2R-trans)-(2-naphthalenyl) [3-[2-(8-phenyloctyl)phenyl]oxiranyl]methanone.

To sodium hydroxide (255 g, 6.37 mol) dissolved in water (650 mL) at 14°-18° C. was added poly-L-leucine (215 g) followed by a mixture of the compound of Example 5a (250 g, 0.531 mol) and n-hexane (4.0 L). The heterogeneous mixture was stirred at ambient temperature for 16 h, then cooled to 10°-15° C. in an ice bath. Ethylenediaminetetraacetic acid disodium salt dihydrate (5 g) was added followed by hydrogen peroxide (H$_2$O$_2$ 30% in water, 1.126 L, 10.93 mol) at such a rate that the reaction temperature did not exceed 25° C. The flow of the hydrogen peroxide was directed below the surface of the reaction by a polypropylene tube attached to the dropping funnel. This addition required 2-3 h. The reaction was stirred at 20°-24° C. for 20 h. The reaction was treated with ethyl acetate (300 mL), and the reaction mixture filtered through a jacketed bench Buchner funnel (40-50° C.). The precipitate (consisting of poly-L-leucine and some product) was washed with boiling ethyl acetate, then slurried in ethyl acetate (1.5 L) at 40°-50° C. for 10-20 min and refiltered. The combined filtrates were placed in a separatory funnel and washed with water (3×500 mL) and brine (1 L). The organic layer was dried (MgSO$_4$, 300 g), filtered, and evaporated (30°- 40° C., 14 mm Hg) to yield a white solid. The product was dissolved in boiling n-hexane-toluene (95:5, 1.90 L), and the hot solution was filtered to remove any insolubles. The solution was kept at ambient temperature for 1.5 h, then placed in a refrigerator at 5° C. for 12 h. The crystalline product was filtered and washed with a small portion of the filtrate and cold hexane (100 mL). The product was air dried for 3 h and then placed in a vacuum desiccator (1 mm Hg, 25° C.) for 24 h, yielding the desired product 200 g (82%), which assayed at 96-97% e.e. by HPLC; mp 62°-63° C.; [α]$_D$+26.6° (c=1.0, CH$_2$Cl$_2$), [α]$_{546}$+31.1°; IR (nujol) 1672, 1403, 1280, 1223, 750 (br), 692 cm$^{-1}$; $^1$H NMR (CDCl$_3$, 360 MHz) δ 8.59 (d, 1 H, J=1.30 Hz), 7.12-8.10 (m, 15 H), 4.36 (d, 1 H, J=1.94 Hz), 4.33 (d, 1 H, J=1.94 Hz), 2.66 (m, 2 H), 2.50 (t, 2 H, J=7.75 Hz), 1.42-1.60 (m, 4 H), 1.02-1.19 (m, 8 H); $^{13}$C NMR (CDCl$_3$) δ 193.13, 142.89, 141.47, 136.02, 133.56, 133.00, 132.49, 130.47, 129.72, 129.37, 129.06, 128.93, 128.55, 128.39, 128.22, 127.91, 127.12, 126.47, 125.56, 124.31, 123.69, 60.48, 57.67, 35.85, 32.73, 31.18, 29.39, 29.18, 29.10; TLC R$_f$ 0.35 (CHCl$_3$, Silica gel GF), 0.43 (CH$_2$Cl$_2$:n-hexane, 3:1); HPLC RT 12.1 min (2R-enantiomer), 18.8 min (2S-enantiomer) (OP(+); 25 cm×4.6 mm; CH$_3$OH; 0.8 mL/min; UV detection at 231 nm), RT 6.0 min (Waters μ-Bondapak ® C-18; 30 cm×3.9 mm; CH$_3$CN:water, 9:1; 2 mL/min; UV detection at 211 nm). Anal. Calcd for C$_{33}$H$_{34}$O$_2$: C, 85.67; H, 7.40. Found C, 85.93; H, 7.48.

c) Preparation of (2R-trans)-(2-naphthalenyl) 3-[2-(8-phenyloctyl)phenyl]oxiranecarboxylate.

To a solution of 3-chloroperbenzoic acid (85%, 28 g, 0.162 mol) in methylene chloride (300 mL) was added (2R-trans)-(2-naphthalenyl) [3-[2-(8-phenyloctyl)-phenyl]oxiranyl]methanone (29 g, 0.062 mol) from Example 5b. The solution was stirred at reflux for 4 h, cooled to 15° C., and the precipitated 3-chlorobenzoic acid was removed by filtration. The solvent was evaporated at <35° C., and the thick residue dissolved in hot isopropanol:toluene (9:1, 300 ml), and allowed to reach room temperature. The mixture was cooled in the refrigerator for 20 h, and the product filtered and dried (25° C., 0.1 mm Hg) to give the desired ester, 25 g (81%), >99.8% e.e. by HPLC. Mp 82°-83° C.; [α]$_D$ −89.5 (c 1, CH$_2$Cl$_2$), [α]$_{546}$ −109.9; IR (nujol) 1752 (s), 1370, 1247, 1210, 1177 (br), 890, 740, 750 cm$^{-1}$; (KBr) 2920, 2850, 1762 (s), 1469, 1337, 1216, 1183, 900, 809, 746, 699 cm$^{-1}$; $^1$H NMR (CDCl$_3$, 360 MHz) δ 7.14-7.91 (m, 16 H), 4.49 (d, 1 H, J=1.51 Hz, oxirane proton), 3.70 (d, 1 H, J=1.72 Hz, oxirane proton), 2.80 (m, 2 H), 2.56 (t, 2 H, J=7.72 Hz), 1.64 (m, 4 H), 1.34 (br, 8 H); $^{13}$C NMR (CDCl$_3$) δ 67.05, 147.88, 142.81, 141.43, 133.70, 132.61, 131.68, 29.65, 129.38, 128.69, 128.34, 128.18, 127.82, 127.71, 126.80, 126.40, 126.01, 125.53, 124.45, 120.43, 118.30, 56.60, 56.22, 35.90, 32.89, 31.38, 31.19, 29.61, 29.45, 29.28; TLC R$_f$ 0.55 (CHCl$_3$, Silica gel GF); HPLC RT 7.25 min (Waters μ-Bondapak® C-18; 30 cm×3.9 mm; CH$_3$CN:water, 9:1; 2 mL/min; UV detection at 220 nm); RT 25.7 min, (2R-enantiomer); 30.46 min (2S-enantiomer); (OP(+); 25 cm×4.5 mm; CH$_3$OH; 0.50 mL/min; UV detection at 220 nm). Anal. Calcd for C$_{33}$H$_{34}$O$_3$: C, 82.80; H, 7.20. Found: C, 82.92; H, 7.09.

EXAMPLE 6

Preparation of (2S-trans)-2-naphthalenyl 3-2-(8-phenyloctyl)phenyl]oxiranecarboxylate a) Preparation of (2S-trans)-(2-naphthalenyl) [3-[2-(8-phenyloctyl)phenyl]oxiranyl]methanone.

To a suspension of poly-D-leucine (3.7 g) in n-hexane (90 mL) and hydrogen peroxide (H$_2$O$_2$ 30% in water, 84 mL) cooled to 10° C. was added sodium hydroxide (5.83 g, 0.146 mol) in water (12 mL). After 80 min, (E)-1-(2-naphthalenyl)-3-[2-(8-phenyloctyl)phenyl]-2-propen-1-one (5.0 g, 11.2 mmol) (Example 5a) was added to the reaction. After stirring for 2 h the cooling bath was removed and the reaction was stirred at room temperature for 52 h. Additional hydrogen peroxide (10 mL) was added, and the reaction continued until TLC indicated little of the starting material remained (144 h). The polymer was filtered, slurried in hot ethyl acetate (50 mL), and refiltered. The aqueous filtrate was extracted with ethyl acetate (3×) and the combined organic layers washed with brine, dried (MgSO$_4$), and evaporated to yield an off-white waxy solid. Recrystallization from boiling hexane/toluene (57 mL/ 68 mL) and vacuum drying yielded 2.96 g (57.3%) of the titled oxiranylmethanone, mp 59°–62° C.; [α]−23.3° (c 1, CH$_2$Cl$_2$); TLC R$_f$ 0.35 (CHCl$_3$, Silica gel GF), 0.43 (CH$_2$Cl$_2$:n-hexane, 3:1); HPLC RT 18.8 min (2S-enantiomer), 12.1 min (2R-enantiomer) (OP(+); 25 cm×4.6 mm; CH$_3$OH; 0.8 mL/min; UV detection at 231 nm), RT 19.7 min (Waters μ-Bondapak® C-18, 30 cm×3.9 mm; CH$_3$CN:water, 85:15; 1.5 mL/min; UV detection at 231 nm). Anal. Calcd for C$_{33}$H$_{34}$O$_2$: C, 85.67; H, 7.40. Found: C, 86.07; H, 7.65.

b) Preparation of (2S-trans)-(2-naphthalenyl) 3[2-(8-phenyloctyl)phenyl]oxiranecarboxylate.

(2S-trans)-(2-naphthalenyl) [3-[2-(8- phenyloctyl) phenyl]oxiranyl]methanone from Example 6a (2.74 g, 5.93 mmol) and 3-chloroperbenzoic acid (85%, 2.47 g, 12.1 mmol) were dissolved in methylene chloride (25 mL) and warmed to 30° C. for 6 h. The reaction was concentrated and dissolved in a hot solution of isopropanol:toluene (10:1, 56 mL), then cooled in the refrigerator. The product was filtered and dried (25° C., 0.1 mm Hg), to yield 2.09 g (74%) of the 2Senantiomer. Mp 82°–83° C.; [α]$_D$+87.2° (c 1.0, CH$_2$Cl$_2$), [α]$_{546}$ +91.9°; Anal. Calcd for C$_{33}$H$_{34}$O$_3$: C, 82.80; H, 7.20. Found: C, 82.96; H, 7.05.

EXAMPLE 7

Preparation of racemic trans-2-naphthalenyl 3-[2-(8-phenyloctyl)phenyl]oxiranecarboxylate a) Preparation of trans-(2-naphthalenyl) [3-[2-(8-phenyloctyl)phenyl]oxiranyl]methanone.

The propen-1-one from Example 5a (0.18 g, 0.446 mmol) in toluene (20 mL) was treated with a cooled solution of sodium hydroxide (2.2 g, 55 mmol) in hydrogen peroxide (H$_2$O$_2$ 30% in water, 3.0 mL, 97 mmol), and Aliquat 336 (tricaprylylmethylammonium chloride, 0.05 g) was added. The solution was stirred at ambient temperature for 16 h, and then hydrogen peroxide (1.0 mL, 32 mmol) was added and the reaction stirred for an additional 2 h. The reaction was treated with diethyl ether (20 mL) and water (20 mL), and the layers separated. The combined organic layers were washed with brine, dried (MgSO$_4$), and evaporated to a solid. The racemic oxiranylmethanone was crystallized from boiling hexane to give a white solid 1.10 g (53%): mp 75°–76° C.; TLC R$_f$ 0.43 (CH$_2$Cl$_2$:n-hexane, 3:1, Silica gel GF); HPLC RT 11.7 min (Waters μ-Bondapak® C-18; 30 cm×3.9 mm; CH$_3$CN:water, 85:15; 1.5 mL/min; UV detection at 230 nm), RT 12.1 min (2R-enantiomer); 18.8 min (2S-enantiomer) (OP(+); 25 cm×4.6 mm; CH$_3$OH; 0.8 mL/min; UV detection at 230 nm).

b) Preparation of trans-2-naphthalenyl 3-[2-(8-phenyloctyl)phenyl]oxiranecarboxylate.

The racemic oxiranylmethanone of Example 7a (0.75 g, 1.62 mmol) in methylene chloride (9 mL) was treated with 3-chloroperbenzoic acid (85%, 0.75 g, 4.3 mmol) and the solution refluxed for 4.5 h. The reaction was cooled to 10° C. and the 3-chlorobenzoic acid filtered. The filtrate was evaporated and the crude white solid crystallized from ethyl alcohol to yield the desired racemic ester (0.505 g, 65%). Mp 67°–68° C.; HPLC RT 26.03 min (2R-enantiomer); 30.47 min (2S-enantiomer) (OP(+); 25 cm×4.6 mm; CH$_3$OH; 0.8 mL/min; UV detection at 231 nm); Anal. Calcd for C$_{33}$H$_{34}$O$_3$: C, 82.80; H, 7.20. Found: C, 82.43; H, 7.22.

EXAMPLE 8

Preparation of (2S-trans)-3-[2-(8phenyloctyl)phenyl]oxiranecarboxamide

The ester of Example 6b, (2S-trans)-2-naphthalenyl 3-[2-(8-phenyloctyl)phenyl]oxiranecarboxylate (2.03 g, 4.2 mmol), in methanol (21 mL) was cooled to 5° C. and a solution of ammonia saturated methanol (20 mL) was added dropwise. After stirring for 5 h at 10°–15° C., the solution was evaporated. The residue was dissolved in toluene and evaporated to a solid. The solid was dissolved in toluene and washed with water, NaOH (10%), water, and finally brine. After drying (MgSO$_4$) and evaporation, the residue was dissolved in boiling hexane CH$_2$Cl$_2$ (8:2), filtered and allowed to stand at 20° C. for 4 h. The solid was collected and dried (0.1 mm Hg, 25° C.) to yield the titled oxiranecarboxamide 1.11 g (76%): mp 80°–82° C.; [α]$_D$ −8.3° (c 1, CH$_2$Cl$_2$); HPLC RT 5.48 min (2S-enantiomer); 9.99 min (2R-enantiomer) (Bakerbond Chiracel OC; 25 cm×4.6 mm; hexane:isopropanol, 1:1; 1.0 mL/min; UV detection at 211 nm); HPLC showed the product at >99% e.e. Anal. Calcd for C$_{23}$H$_{29}$O$_2$N: C, 78.59; H, 8.32; N, 3.99. Found: C, 78.35; H, 8.34; N, 3.90.

EXAMPLE 9

Preparation of (2R-trans)-1-naphthalenyl 3-[2-(4-phenoxybutyl)phenyl]oxiranecarboxylate a) Preparation of (E)-1-(1-naphthalenyl)-3-[2-(4-phenoxybutyl)phenyl]-2-propen-1-one. Using the method of Example 5a, 1'-acetonaphthone is reacted with 2-(4-phenoxybutyl)benzaldehyde in alcohol solution to give the titled compound.

b) Preparation of (2R-trans)-(1-naphthalenyl) [3-[2-(4-phenoxybutyl)phenyl]oxiranyl]methanone.

Using the method of Example 5b, the compound from example 9a is reacted with poly-L-alanine, potassium hydroxide, hydrogen peroxide (30% aqueous), and ethylenediaminetetraacetic acid in a cyclohexane/water mixture to give the titled epoxy ketone.

c) Preparation of (2R-trans)-1-naphthalenyl 3-[2-(4-phenoxybutyl)phenyl]oxiranecarboxylate.

Using the method of Example 5c, the epoxy ketone of Example 9b is reacted with 3-chloroperbenzoic acid in methylene chloride to yield the titled epoxy ester.

EXAMPLE 10

Preparation of (2R-trans)-2-naphthalenyl 3-[(2-(dodecyl)phenyl]oxiranecarboxylate a) Preparation of (E)-1-(2-naphthalenyl)-3-[2-(dodecyl)phenyl]-2-propen-1-one.

Using the method of Example 5a, 2-acetonaphthone is reacted with 2-dodecylbenzaldehyde to give the titled compound.

b) Preparation of (2R-trans)-(2-naphthalenyl)[3-[(2-dodecyl)phenyl]oxiranyl]methanone.

Using the method of Example 5b, the compound of Example 10a is reacted with poly-L-alanine, potassium hydroxide, ethylenediaminetetraacetic acid and hydrogen peroxide in cyclohexane to give the titled epoxy ketone.

c) Preparation of (2R-trans)-2-naphthalenyl 3-[(2-dodecyl)phenyl]oxiranecarboxylate.

Using the method of Example 5c, the compound of Example 10b is reacted with 3-chloroperbenzoic acid in chloroform to yield the titled epoxy ester.

EXAMPLE 11

Preparation of (2R-trans-2,4-dimethylphenyl 3-[2-(12,12,12-trifluorododecyl)phenyl]oxiranecarboxylate a) Preparation of (E)-1-(2,4-dimethylphenyl)-3-[2-(12,12,12-trifluorododecyl) phenyl]-2-propen-1-one.

Using the method of Example 5a, 2,4-dimethylacetophenone is reacted with 2-(12,12,12-trifluorododecyl)benzaldehyde to give the titled compound.

b) Preparation of (2R-trans)-(2,4dimethylphenyl) [3-[2-(12,12,12-trifluorododecyl)) phenyl]oxiranyl]methanone.

Using the method of Example 5b, the compound of Example 11a is reacted with poly-L-alanine, sodium hydroxide and hydrogen peroxide to give the titled epoxy-ketone.

c) Preparation of (2R-trans)-2,4-dimethylphenyl 3-[2-(12,12,12-trifluorododecyl)phenyl]oxiranecarboxylate.

Using the method of Example 5c, the compound of Example 11b is reacted with perbenzoic acid in methylene chloride to yield the titled epoxy-ester.

EXAMPLE 12

Preparation (2R-trans)-2-naphthalenyl 3-(2-(undecyloxy)phenyl]oxiranecarboxylate a) Preparation of (E)-1-(2-naphthalenyl)-3-[2-undecyloxyphenyl)phenyl]-2-propen-1-one.

Using the method of Example 5a, 2-acetonaphthone is reacted with 2-undecyloxybenzaldehyde to give the titled compound.

b) Preparation of (2R-trans)-(2-naphthalenyl) [3-[2-(undecyloxy)phenyl]oxiranyl]methanone.

Using the method of Example 5b, the compound of Example 12a is reacted with poly-L-alanine, lithium hydroxide and hydrogen peroxide to give the titled epoxy-ketone.

c) Preparation of (2R-trans)-2-naphthalenyl 3-[2-(undecyloxy)phenyl] oxiranecarboxylate.

Using the method of Example 5c, the compound of Example 12b is reacted with 3-chloroperbenzoic acid in methylene chloride to yield the titled epoxy-ester.

EXAMPLE 13

Preparation of (2R-trans)-2,4-dichlorophenyl 3-[2-(8phenyloctyl)-5-(trifluoromethyl)phenyl]oxiranecarboxylate a) Preparation of (E)-1-(2,4-dichlorophenyl)-3-[2-(8-phenyloctyl)-5-(trifluoromethyl)phenyl]-2-propen-1-one.

Using the method of Example 5a, 2,4-dichloroacetophenone is reacted with 2-(8-phenyloctyl)-5-trifluoromethyl-benzaldehyde to give the titled compound.

b) Preparation of (2R-trans)-(2,4-dichlorophenyl) [3-[2-(8-phenyloctyl)-5-(trifluoromethyl)phenyl]oxiranyl]methanone.

Using the method of Example 5b, the compound of Example 13a is reacted with poly-L-alanine, potassium hydroxide and t-butyl hydroperoxide to give the titled epoxy-ketone.

c) Preparation of (2R-trans)-2,4-dichlorophenyl 3-[2-(8-phenyloctyl)-5-(trifluoromethyl)phenyl]oxiranecarboxylate.

Using the method of Example 5c, the compound of Example 13b is reacted with 3-chloroperbenzoic acid in methylene chloride to yield the titled epoxy-ester.

EXAMPLE 14

Preparation of (2R-trans)-2-naphthalenyl 3-[2-[(8-cyclohexyl)octyl]phenyl]oxiranecarboxylate a) Preparation of (E)-1-(2-naphthalenyl)-3-[(2-(8-cyclohexyl)octyl]phenyl]-2-propen-1-one Using the method of Example 5a, 2-acetonaphthone is reacted with 2-(8-cyclohexyloctyl)benzaldehyde to give the titled compound.

b) Preparation of (2R-trans)-(2-naphthalenyl) [3-[2-[(8-cyclohexyl)octyl]phenyl]oxiranyl]methanone.

Using the method of Example 5b, the compound of Example 14a is reacted with poly-L-alanine, potassium hydroxide and hydrogen peroxide to give the titled epoxy-ketone.

c) Preparation of (2R-trans)-2-naphthalenyl 3-[2-[(8-cyclohexyl)octyl]phenyl]oxiranecarboxylate.

Using the method of Example 5c, the compound of Example 14b is reacted with 3-chloroperbenzoic acid in methylene chloride to yield the titled epoxy-ester.

EXAMPLE 15

Preparation of (2R-trans)-2-naphthalenyl 3-[3-(6-phenylhexyl)phenyl]oxiranecarboxylate a) Preparation of (E)-1-(2-naphthalenyl)-3-[3-(6-phenylhexyl)phenyl]-2-propen-1-one.

Using the method of Example 5a, 2-acetonaphthone is reacted with 3-(6-phenylhexyl)benzaldehyde to give the titled compound.

b) Preparation of (2R-trans)-(2-naphthalenyl) [3-[3-(6-phenylhexyl)phenyl]oxiranyl]methanone.

Using the method of Example 5b, the compound of Example 15a is reacted with poly-L-alanine, potassium hydroxide and hydrogen peroxide to give the titled epoxy-ketone.

c) Preparation of (2R-trans)-2-naphthalenyl 3-[3-(6-phenylhexyl)phenyl]oxiranecarboxylate.

Using the method of Example 5c, the compound of Example 15b is reacted with 3-chloroperbenzoic acid in methylene chloride to yield the titled epoxy-ester.

EXAMPLE 16

Preparation (2R-trans)-4-methoxyphenyl 3-[5-nitro-2-undecyloxy)phenyl]oxiranecarboxylate a) Preparation of (E)-1-(4-methoxyphenyl)-3-[5-nitro-2-(undecyloxy)phenyl]-2-propen-1-one.

Using the method of Example 5a, 2-acetonaphthone is reacted with 2-undecyloxy-5-nitro-benzaldehyde to give the titled compound.

b) Preparation of (2R-trans)-(4-methoxyphenyl) [3-[5-nitro-2-(undecyloxy) phenyl]oxiranyl]methanone.

Using the method of Example 5b, the compound of Example 16a is reacted with poly-L-alanine, potassium hydroxide and hydrogen peroxide in a toluene/water mixture to give the titled epoxy-ketone.

c) Preparation of (2R-trans)-4-methoxyphenyl 3-[5-nitro-2-(undecyloxy)phenyl]oxiranecarboxylate.

Using the method of Example 5c, the compound of Example 16b is reacted with 3-chloroperbenzoic acid in methylene chloride to yield the titled epoxy-ester.

EXAMPLE 17

Preparation of (2R-trans)-2,4-dimethylphenyl 3-[2-[8-(2-furyl)octyl]phenyl]oxiranecarboxylate Preparation of (E)-1-(2,4-dimethylphenyl)-3-[2-[8-(2-furyl)octyl]phenyl]-2-propen-1-one.

Using the method of Example 5a, 2,4-dimethylacetophenone is reacted with 2-(8-(2-furyl)octyl)benzaldehyde to give the titled compound.

b) Preparation of (2R-trans)-(2,4-dimethylphenyl) [3-[2-[8-(2-furyl)octyl]phenyl]oxiranyl]methanone.

Using the method of Example 5b, the compound of Example 17a is reacted with poly-L-alanine, sodium hydroxide and hydrogen peroxide in a carbon tetrachloride water mixture to give the titled epoxy-ketone.

c) Preparation of (2R-trans)-2,4-dimethylphenyl 3-[2-[8-(2-furyl)octyl]phenyl]oxiranecarboxylate.

Using the method of Example 5c, the compound of Example 17b is reacted with perbenzoic acid in methylene chloride to yield the titled epoxy-ester.

EXAMPLE 18

Preparation of (2R-trans)-2-naphthalenyl 3-[3-(nonyloxy) phenyl]oxiranecarboxylate a) Preparation of (E)-1-(2-naphthalenyl)-3-[3-(nonyloxy)phenyl]-2-propen-1-one.

Using the method of Example 5a, 2-acetonaphthone is reacted with 3-nonyloxybenzaldehyde to give the titled compound.

a) Preparation of (2R-trans)-2-naphthalenyl [3-(nonyloxy)phenyl]oxiranyl]methanone.

Using the method of Example 5b, the compound of Example 18a is reacted with poly-L-alanine, lithium hydroxide and hydrogen peroxide to give the titled epoxy-ketone.

c) Preparation of (2R-trans)-2-naphthalenyl 3-[3-(nonyloxy)phenyl]oxiranecarboxylate.

Using the method of Example 5c, the compound of Example 18b is reacted with 3-chloroperbenzoic acid in methylene chloride to yield the titled epoxy-ester.

EXAMPLE 19

Preparation of (2R-trans)-2,4-dichlorophenyl 3-[2-5-bromo-6-(4-methylphenyl)hexyl]phenyl]oxiranecarboxylate a) Preparation of (E)-1-(2,4-dichlorophenyl)-3-[[2-(6(4-methylphenyl)hexyl)-5(bromo)]phenyl]-2-propen-1-one.

Using the method of Example 5a, 2,4-dichloroacetophenone is reacted with 2-(4-methylphenyl)hexyl-5-bromo)-benzaldehyde to give the titled compound.

b) Preparation of (2R-trans)-(2,4-dichlorophenyl) [3-[2-[5-bromo-6-(4-methylphenyl) hexyl]phenyl]oxiranyl]methanone.

Using the method of Example 5b, the compound of Example 19a is reacted with poly-L-leucine, potassium hydroxide and t-butyl hydroperoxide to give the titled epoxy-ketone.

c) Preparation of (2R-trans)-2,4-dichlorophenyl 3-[2-[5-bromo-6-(4-methylphenyl) hexyl]phenyl]oxiranecarboxylate.

Using the method of Example 5c, the compound of Example 19b is reacted with 3-chloroperbenzoic acid in methylene chloride to yield the titled epoxy-ester.

EXAMPLE 20

Preparation of (2R-trans)-2-naphthalenyl 3-[2-[7-(4-chlorophenyl)heptyl]-5-(methyl)phenyl]oxiranecarboxylate a) Preparation of (E)-1-(2-naphthalenyl)-3-[2-[7-(4-chlorophenyl)heptyl]-5-(methyl)phenyl]-2propen-1-one.

Using the method of Example 5a, 2-acetonaphthone is reacted with 2-[7-(4-chlorophenyl)heptyl)-5-methylbenzaldehyde to give the titled compound.

b) Preparation of (2R-trans)-(2-naphthalenyl) [3-[2-[7-(4-chlorophenyl)heptyl]-5-(methyl)phenyl]oxiranyl]methanone Using the method of Example 5b, the compound of Example 20a is reacted with poly-L-leucine, potassium hydroxide and hydrogen peroxide in a petroleum ether/water mixture to give the titled epoxy-ketone.

c) Preparation of (2R-trans)-2-naphthalenyl 3-[2-[7-(4-chlorophenyl)heptyl]-5-(methyl)phenyl]oxiranecarboxylate.

Using the method of Example 5c, the compound of Example 20b is reacted with 3-chloroperbenzoic acid in methylene chloride to yield the titled epoxy-ester.

EXAMPLE 21

Preparation of (2R-trans)-3-trifluoromethylphenyl 3-[2-[8-(4-methylphenyl)-3-[2-[8-(4-methoxyphenyl)octyl]phenyl]2-propen-1-one.

Using the method of Example 5a, 3-trifluoromethylacetophenone is reacted with 2-(8-(4-methoxyphenyl)octyl)benzaldehyde to give the titled compound.

b) Preparation of (2R-trans)-(3-trifluoromethylphenyl) [3-[2-[8-(4-methoxyphenyl)octyl]phenyl]oxiranyl]methanone.

Using the method of Example 5b, the compound of Example 21a is reacted with poly-L-alanine, potassium hydroxide and hydrogen peroxide to give the titled epoxy-ketone.

c) Preparation of (2R-trans)-3-trifluoromethylphenyl 3-[2-[8-(4-methoxyphenyl) octyl]phenyl]oxiranecarboxylate.

Using the method of Example 5c, the compound of Example 21b is reacted with 3-chloroperbenzoic acid in methylene chloride to yield the titled epoxy-ester.

EXAMPLE 22

Preparation of (2R-trans)-4-ethylphenyl 3-[2-[10-(2,4-dimethylphenyl)decyl]-3-(nitro)phenyl]oxiranecarboxylate a) Preparation of (E)-1-(4-ethylphenyl)-3-[2-[10-(2,4-dimethylphenyl)decyl]-3-(nitro)phenyl]-2-propen-1-one.

Using the method of Example 5a, (4-ethylphenyl)acetophenone is reacted with 2-[10-(2,4-dimethylphenyl)decyl]-benzaldehyde to give the titled compound.

b) Preparation of (2R)-trans-(4-ethylphenyl) [3-[2-[10-(2,4-dimethylphenyl)decyl]-3(nitro)phenyl]oxiranyl]methanone.

Using the method of Example 5b, the compound of Example 22a is reacted with poly-L-alanine, sodium hydroxide and hydrogen peroxide to give the titled epoxy-ketone.

c) Preparation of (2R-trans)-4-ethylphenyl 3-[2-[10-(2,4-dimethylphenyl)decyl]-3-(nitro)phenyl]oxiranecarboxylate.

Using the method of Example 5c, the compound of Example 22b is reacted with 3-chloroperbenzoic acid in methylene chloride to yield the titled epoxy-ester.

EXAMPLE 23

Preparation of (2R-trans-1-naphthalenyl 3-[2-(8-(2-thienyl)octyl]-3-(trifluoromethyl)phenyl]oxiranecarboxylate a) Preparation of (E)-1-(1-naphthalenyl)-3-[2-[8-(2-thienyl)octyl]-3-(trifluoromethyl) phenyl]-2-propen-1-one.

Using the method of Example 5a, 1-acetonaphthone is reacted with 2-[8-(2-thienyl)octyl]-3-trifluoromethylbenzaldehyde to give the titled compound.

Preparation of (2R-trans)-(1-naphthalenyl) [3-[2-[8-(2-thienyl)octyl]-3-(trifluoromethyl)phenyl]oxiranyl]methanone.

Using the method of Example 5b, the compound of Example 23a is reacted with poly-L-leucine, sodium hydroxide and hydrogen peroxide to give the titled epoxy-ketone.

c) Preparation of (2R-trans)-1-naphthalenyl 3-[2-[8-(2-thienyl)octyl]-3-(trifluoromethyl)phenyl]oxiranecarboxylate.

Using the method of Example 5c, the compound of Example 23b is reacted with 3-chloroperbenzoic acid in methylene chloride to yield the titled epoxy-ester.

EXAMPLE 24

Preparation of (2R-trans)-2-bromophenyl 3-[2-[8-[(3-trifluoromethyl)phenyl]octyl]phenyl]oxiranecarboxylate a) Preparation of (E)-1-(2-bromophenyl)-3-[2-[8-[(3-trifluoromethyl)phenyl]octyl]phenyl]-2-propen-1-one.

Using the method of Example 5a, 2-bromoacetophenone is reacted with 2-[8-(3-trifluoromethylphenyl)octyl]benzaldehyde to give the titled compound.

b) Preparation of (2R-trans)-(2-bromophenyl) [3-[2-[8-[(3-trifluoro-methyl)phenyl]octyl]phenyl]oxiranyl]methanone.

Using the method of Example 5b, the compound of Example 24a is reacted with poly-L-leucine, potassium hydroxide and hydrogen peroxide to give the titled epoxy-ketone.

c) Preparation of (2R-trans)-2-bromophenyl 3-[2-[8-[(3-trifluoromethyl)phenyl]octyl]phenyl]oxiranecarboxylate.

Using the method of Example 5c, the compound of Example 24b is reacted with 3-chloroperbenzoic acid in methylene chloride to yield the titled epoxy-ester.

EXAMPLE 25

Preparation of (2R-trans)-3-[2-(8-phenyloctyl)phenyl]oxiranecarboxamide

The ester of Example 5c (2R-trans)-(2-napthhalenyl) 3-[2-(8-phenyloctyl)phenyl]oxiranecarboxylate (462 g, 1 mol) was dissolved in acetone (5 L) and ammonium hydroxide (1 L). After stirring briefly at room temperature the reaction mixture was heated to reflux for 20 minutes, recooled to room temperature and concentrated to ⅓ of the original volume on the rotary evaporator. The solution was diluted with toluene (10 L) and washed with 10% aq. NaOH (3×5 L), water (1×5 L) and brine (1×5 L). The toluene solution was further evaporated to a volume of 2.5 L and n-hexane (7.5 L) was added. Upon cooling in the refrigerator (~12 h), the solid was collected and dried to yield the titled oxiranecarboxamide (302 g, 86%). Mp 81°–82° C.; $[\alpha]_D$ +13.2° (c 1, $CH_2Cl_2$, 25° C.), $[\alpha]_{546}$ +16.1.

EXAMPLE 26

Preparation of D-leucine homopolymer a) Preparation of NCA-D-Leucine.

D-Leucine (25.0 g, 0.191 mol) in dry tetrahydrofuran (300 mL) was degassed with nitrogen for 5 min. The solution was cooled to 0°–5° C., and the flask was equipped with a condenser maintained at −5° C. A stream of phosgene was passed through the reaction until 35 g (0.354 mol) had been added. The cooling bath was removed and the reaction allowed to reach 25° C. The reaction was stirred at 50°–60° C. for 2 h, and stirred at 25° C. for an additional 2 h. The reaction was degassed with nitrogen, concentrated at 30° C., and dissolved in hexane:toluene (125:100 mL), and cooled to 5° C. for 16 h. The product was filtered and dried (25° C. at 0.1 mm Hg). Recrystallization (hexane:toluene, (125:87 mL)) gave after drying, a white solid, 16.79 g (56%), mp 72°–74° C.

b) Preparation of Poly-D-leucine.

The above product was spread on a tray and placed in a humidity chamber (70% humidity, 25° C.). The polymerization of the carboxyanhydride was followed by the disappearance of the anhydride bond in the infrared spectrum (IR). The polymerization was complete by IR after 8 days, yielding the desired homopolymer in quantitative yield.

Based upon this disclosure many variations and modifications of these procedures will be apparent to those skilled in the chemical arts. Such modifications are intended to be comprehended within the scope of this invention and the claims which follow.

What is claimed is:

1. An improved process for preparing a chiral α-epoxy ketone of the formula:

wherein
$R_1$ is $(L)_a$—$(CH_2)_b$—$(T)_c$—Q;
a is 0 or 1;
b is 3 to 14;
c is 0 or 1;
L and T are independently oxygen or $CH_2$;
Q is $C_{1-4}$alkyl, trifluoromethyl, furanyl, thienyl, cyclohexyl or phenyl, optionally monosubstituted with Br, Cl, $CF_3$, $C_{1-4}$alkoxy, or $C_{1-4}$alkyl;
$R_2$ and A are independently selected from H, $CF_3$, $C_{1-4}$alkyl, halogen or $NO_2$;
or $R_1$ is H and $R_2$ is $(L)_a$—$(CH_2)_b$—$(T)_c$—Q
wherein a, b, c, L, T and B are as defined above; and
$R_3$ is phenyl or naphthyl unsubstituted or substituted by one or two halogen, $C_{1-4}$alkyl, $C_{1-4}$alkoxy or trifluoromethyl groups;
comprising reacting an α,β-unsaturated ketone of the formula:

wherein $R_1$, $R_2$, A and $R_3$ are defined above, with a polyamino acid, an oxidant and a base in a mixture of water and an organic solvent wherein the improvement is the use of a nonaromatic and non-chlorinated hydrocarbon solvent.

2. A process according to claim 1 in which the hydrocarbon solvent is a $C_{3-8}$ straight or branched chain alkane or cycloalkane or a suitable petroleum ether.

3. A process according to claim 2 in which the hydrocarbon solvent is hexane.

4. A process according to claim 3 in which the polyamino acid, the base and the α,β-unsaturated ketone are stirred for a time from about 1 hour to about 72 hours prior to the addition of the hydrogen peroxide.

5. A process according to claim 4 in which the time is 12 to 48 hours.

6. A process according to claim 4 which further comprises a metal chelator.

7. A process according to claim 4 in which the polyamino acid is polyalanine or polyleucine.

8. A process according to claim 6 in which the metal chelator is EDTA.

9. A process according to claim 7 in which the oxidant is hydrogen peroxide.

10. A process according to claim 9 in which the polyamino acid is poly-L-leucine.

11. A process according to claim 10 in which $R_3$ is naphthyl and $R_1$ is phenyloctyl.

12. A process for preparing a compound of the formula:

wherein
$R_1$ is $(L)_a$—$(CH_2)_b$—$(T)_c$—Q;
a is 0 or 1;
b is 3 to 14;
c is 0 or 1;
L and T are independently oxygen or $CH_2$;
Q is $C_{1-4}$alkyl, trifluoromethyl, furanyl, thienyl, cyclohexyl or phenyl, optionally monosubstituted with Br, Cl, $CF_3$, $C_{1-4}$alkoxy, or $C_{1-4}$alkyl;
$R_2$ and A are independently selected from H, $CF_3$, $C_{1-4}$alkyl, halogen or $NO_2$;
or $R_1$ is H and $R_2$ is $(L)_a$—$(CH_2)_b$—$(T)_c$—Q,
wherein a, b, c, L, T and Q are as defined above; and
$R_3$ is phenyl or naphthyl unsubstituted or substituted by one or two halogen, $C_{1-4}$alkyl, $C_{1-4}$alkoxy or trifluoromethyl groups;
which comprises:
reacting an α-epoxy ketone of the formula:

wherein the substituents, $R_1$, $R_2$, $R_3$ and A are defined as above for formula (IV), with a peracid.

13. A process according to claim 12 in which the peracid is perbenzoic acid or 3-chloroperbenzoic acid.

14. A process according to claim 13 in which the peracid is 3-chloroperbenzoic acid.

15. A process according to claim 14 which is conducted in a methylene chloride, 1,2-dichloroethane, hexane, ethyl acetate or chloroform solvent.

16. A process according to claim 15 which is conducted at about the reflux temperature of the solvent.

17. A process according to claim 16 in which $R_3$ is naphthyl and $R_1$ is phenyloctyl.

18. A process for preparing an α-epoxy ester of the formula:

wherein
$R_1$ is $(L)_a$—$(CH_2)_b$—$(T)_c$—Q;
a is 0 or 1;
b is 3 to 14;
c is 0 or 1;
L and T are independently oxygen or $CH_2$;

Q is $C_{1-4}$alkyl, trifluoromethyl, furanyl, thienyl, cyclohexyl or phenyl, optionally monosubstituted with Br, Cl, $CF_3$, $C_{1-4}$alkoxy, or $C_{1-4}$alkyl;

$R_2$ and A are independently selected from H, $CF_3$, $C_{1-4}$alkyl, halogen or $NO_2$;

or $R_1$ is H and $R_2$ is $(L)_a$—$(CH_2)_b$—$(T)_c$—Q, wherein a, b, c, L, T and Q are as defined above; and $R_3$ is phenyl or naphthyl unsubstituted or substituted by one or two halogen, $C_{1-4}$alkyl, $C_{1-4}$alkoxy or trifluoromethyl groups;

which comprises:

(a) reacting an α,β-unsaturated ketone of the formula:

(II)

wherein the substituents $R_1$, $R_2$, $R_3$ and A are defined as above in formula (IV), with an oxidant in the presence of a base to yield an α-epoxy ketone; and (b) reacting the α-epoxy ketone with a peracid to yield a compound of formula (IV).

19. A process according to claim 18 which further comprises the addition of a polyamino acid in step (a).

20. A process according to claim 19 in which step (a) is conducted in a mixture of an organic solvent and water.

21. A process according to claim 20 in which the oxidant is hydrogen peroxide.

22. A process according to claim 21 in which the base is an alkali metal hydroxide, alkali metal carbonate or a tetraalkyl ammonium hydroxide.

23. A process according to claim 22 which further comprises adding a metal chelator in step (a).

24. A process according to claim 22 in which the polyamino acid is polyalanine or polyleucine.

25. A process according to claim 23 in which the metal chelator is EDTA.

26. A process according to claim 24 in which the peracid in step (b) is perbenzoic acid or 3-chloroperbenzoic 27. A process according to claim 25 in which the organic solvent in step (a) is hexane, toluene or carbon tetrachloride.

28. A process according to claim 24 in which the polyamino acid and the base are stirred together for a time of 1-72 hours prior to addition of the hydrogen peroxide.

29. A process according to claim 28 in which the time is 12-48 hours.

30. A process according to claim 29 in which the base is an alkali metal hydroxide.

31. A process according to claim 30 in which the organic solvent is hexane.

32. A process according to claim 31 in which the polyamino acid is poly-L-leucine.

33. A process according to claim 32 in which the peracid in step (b) is 3-chloroperbenzoic acid.

34. A process according to claim 33 in which $R_3$ is naphthyl, phenyl, 4-fluorophenyl, 4-methylphenyl or 4-bromophenyl.

35. A process according to claim 34 in which $R_1$ is phenylheptyl, phenyloctyl, phenylnonyl, undecyl, dodecyl, tridecyl, decyloxy, undecyloxy or dodecyloxy.

36. A process according to claim 18 in which A is hydrogen, $R_2$ is hydrogen and $R_1$ is phenyloctyl.

37. A process for the preparation of (2R-trans)-(2-naphthalenyl) 3-[2-(8-phenyloctyl)phenyl]oxirane carboxylate which comprises:

a) reacting (E)-1-(2-naphthalenyl)-3-[2-(8-phenyloctyl)phenyl]-2-propen-1-one with hydrogen peroxide, in the presence of sodium hydroxide, and poly-L-leucine to yield (2R-trans)-(2-naphthalenyl) [3-[2-(8-phenyloctyl)phenyl]oxiranyl]methanone; and b) reacting (2R-trans)-(2-naphthalenyl) [3-[2-(8-phenyloctyl)phenyl]oxiranyl]methanone of step (a) with 3-chloroperbenzoic acid to yield (2R-trans)-(2-naphthalenyl) 3[2-(8-phenyloctyl)phenyl]oxirane carboxylate.

* * * * *